(12) United States Patent
Bandara et al.

(10) Patent No.: US 11,389,796 B2
(45) Date of Patent: Jul. 19, 2022

(54) FLUIDIC DEVICES FOR CHROMATOGRAPHIC SEPARATION AND METHODS OF MAKING AND USING THE SAME

(71) Applicant: Oregon State University, Corvallis, OR (US)

(72) Inventors: Gayan C. Bandara, Corvallis, OR (US); Christopher A. Heist, Decatur, GA (US); Vincent T. Remcho, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 614 days.

(21) Appl. No.: 16/201,646

(22) Filed: Nov. 27, 2018

(65) Prior Publication Data

US 2019/0091688 A1 Mar. 28, 2019

Related U.S. Application Data

(63) Continuation of application No. PCT/US2017/035018, filed on May 30, 2017.

(60) Provisional application No. 62/343,621, filed on May 31, 2016.

(51) Int. Cl.
*B01L 3/00* (2006.01)
*G01N 33/18* (2006.01)

(52) U.S. Cl.
CPC ... *B01L 3/502753* (2013.01); *B01L 3/502707* (2013.01); *G01N 33/1813* (2013.01); *B01L 2200/12* (2013.01); *B01L 2300/0681* (2013.01); *B01L 2300/0803* (2013.01); *B01L 2300/0816* (2013.01); *B01L 2300/0864* (2013.01); *B01L 2300/0887* (2013.01); *B01L 2300/126* (2013.01); *B01L 2300/161* (2013.01); *B01L 2300/165* (2013.01)

(58) Field of Classification Search
CPC .................................. B01L 3/502753
USPC .......................................... 436/80
See application file for complete search history.

(56) References Cited

U.S. PATENT DOCUMENTS

| | | | |
|---|---|---|---|
| 3,730,807 | A | 5/1973 | Smith et al. |
| 8,628,729 | B2 | 1/2014 | Carrilho et al. |
| 2003/0102080 | A1 | 6/2003 | Mallik |
| 2003/0220700 | A1 | 11/2003 | Hammer et al. |

(Continued)

FOREIGN PATENT DOCUMENTS

| | | |
|---|---|---|
| CN | 105548315 A | 5/2016 |
| EP | 2 016 189 | 1/2012 |

(Continued)

OTHER PUBLICATIONS

Spicar-Mihalic et al., "$CO_2$ laser cutting and ablative etching for the fabrication of paper-based devices," J. Micromech. Microeng. 23 (May 13, 2013), 6 pages.

(Continued)

*Primary Examiner* — Christine T Mui
*Assistant Examiner* — Emily R. Berkeley
(74) *Attorney, Agent, or Firm* — Klarquist Sparkman, LLP

(57) ABSTRACT

Disclosed herein are embodiments of fluidic devices that can be used to detect the presence (or absence) of analytes in samples by providing separate and distinct chromatographic signals for particular analytes. The fluidic devices described herein are highly sensitive and user-friendly. Methods of making and using the disclosed fluidic devices also are disclosed herein.

21 Claims, 23 Drawing Sheets

(56) References Cited

U.S. PATENT DOCUMENTS

| | | |
|---|---|---|
| 2004/0037990 A1 | 2/2004 | Abe et al. |
| 2004/0053422 A1 | 3/2004 | Chan et al. |
| 2008/0099064 A1 | 5/2008 | Hayes |
| 2009/0181411 A1 | 7/2009 | Battrell et al. |
| 2011/0011781 A1 | 1/2011 | Blankenstein et al. |
| 2011/0135698 A1 | 6/2011 | Lundquist et al. |
| 2011/0107168 A1 | 8/2011 | Kornev et al. |
| 2011/0272644 A1 | 11/2011 | Remcho et al. |
| 2013/0064713 A1 | 3/2013 | Koesdjojo et al. |
| 2013/0146643 A1 | 6/2013 | Schmid et al. |
| 2014/0106139 A1 | 4/2014 | Abrams |
| 2014/0235510 A1 | 8/2014 | Chang-Yen et al. |
| 2014/0248471 A1 | 9/2014 | Hanschen et al. |
| 2016/0146823 A1 | 5/2016 | Chiu et al. |
| 2016/0158428 A1 | 6/2016 | Charest et al. |
| 2018/0178212 A1 | 6/2018 | Roxhed et al. |
| 2018/0200677 A1 | 7/2018 | Lee |
| 2019/0242870 A1 | 8/2019 | Doi |

FOREIGN PATENT DOCUMENTS

| | | |
|---|---|---|
| WO | WO 2011/072715 | 6/2011 |
| WO | WO 2011/097677 | 8/2011 |
| WO | WO 2012/071629 | 6/2012 |
| WO | WO 2016/172675 | 10/2016 |
| WO | WO 2016/209147 | 12/2016 |

OTHER PUBLICATIONS

Nie et al. "One-step patterning of hollow microstructures in paper by laser cutting to create microfluidic analytical devices," Analyst, Nov. 14, 2012, 138, 671.

Guarino et al., "Polycapralactone: synthesis, properties and applications," Encyclopedia of Polymer Science and Technology, Aug. 15, 2017.

Jenkins et al., "The effect of molecular weight on the crystallization kinetics of polycapralactone," Polymers for Advanced Technologies, vol. 17, pp. 474-478, Jul. 10, 2006.

Lewis et al., "Quantifying analytes in paper-based microfluidic devices without using external electronic readers," Angew. Chem. Int. Ed., 51 (51): 12707-12710, Nov. 9, 2012.

Zhang et al., "Naked-eye quantitative aptamer-based assay on paper device," Biosensors and Bioelectronics, vol. 78, pp. 538-546, Dec. 4, 2015.

"Paper Microzone Plates," NIH 3D Print Exchange: A collection of biomedical 3D printable files and 3D printing resources supported by the National Institutes of Health, accessed at https://3dprint.nih.gov/discover/paper-microzone, Jul. 2014.

Abgrall et al., "Fabrication of planar nanofluidic channels in a thermoplastic by hot-embossing and thermal bonding," Lab Chip, No. 4, pp. 520-522, Jan. 11, 2007.

Allo et al., "Synthesis and Electrospinning of ε-Polycapralactone-Bioactive Glass Hybrid Biomaterials via a Sol-Gel Process," Langmuir, 26(23): 18340-18348, Nov. 4, 2010.

Armani et al., "Microfabrication technology for polycaprolactone, a biodegradable polymer," J. Micromech. Microeng., 10(1): 80-84, Jan. 6, 2000.

Becker et al., "Hot embossing as a method for the fabrication of polymer high aspect ratio structures," Sensors and Actuators, 83(1-3): 130-135, May 22, 2000.

Burgoyne, "Interfacing of microfluidic devices." Chips and Tips, Feb. 27, 2009. rsc.org, blog, downloaded Jun. 27, 2013.

Carrilho et al., "Paper Microzone Plates," Anal. Chem., 81(15): 5990-5998, Jul. 2, 2009.

Chen et al., "Fabrication, modification, and application of poly(methyl methacrylate) microfluidic chips," Electrophoresis, 29(9): 1801-1814, May 9, 2008.

Chen et al., "Vacuum-assisted thermal bonding of plastic capillary electrophoresis microchip imprinted with stainless steel template," Journal of Chromatography A, 1038(1-2): 239-245, Jun. 4, 2004.

Cheow et al., "Antibacterial Efficacy of Inhalable Antibiotic-Encapsulated Biodegradable Polymeric Nanoparticles Against E. coli Biofilm Cells," Journal of Biomedical Nanotechnology, 6(4): 391-403, Aug. 2010.

Christensen et al., "Characterization of interconnects used in PDMS microfluidic systems," Journal of Micromechanics and Microengineering, 15(5): 928-934, Mar. 22, 2005.

Chu et al., "Comparison of polyurethane foam and biodegradable polymer as carriers in moving bed biofilm reactor for treating wastewater with a low C/N ratio," Chemosphere, 83(1): 63-68, Mar. 2011.

Dang et al., "Replica mutilchannel polymer chips with a network of sacrificial channels sealed by adhesive printing method," Lab Chip, vol. 4, pp. 472-478, Feb. 1, 2005.

Davis et al., "Carrier systems and biosensors for biomedical applications," Tissue Engineering Using Ceramics and Polymers: Second Edition, pp. 270-302, 2014.

Esch et al., "Influence of master fabrication techniques on the characteristics of embossed microfluidic channels," Lab Chip, vol. 3, pp. 121-127, May 2, 2003.

Hu et al., "The use of reactive polymer coatings to facilitate gene delivery from poly (ε-caprolactone) scaffolds," Biomaterials, 30(29): 5785-5792, Oct. 2009.

International Search Report and Written Opinion issued for International Application No. PCT/US2017/35018 dated Oct. 3, 2017.

Ishida et al., "Reversed-phase liquid chromatography on a microchip with sample injector and monolithic silica column," Journal of Chromatography A, 1132(1-2): 90-98, Nov. 3, 2006.

Jacobson et al., "Effects of Injection Schemes and Column Geometry on the Performance of Microchip Electrophoresis Devices," Anal. Chem., 66(7): 1107-1113, Apr. 1994.

Jain et al., "Performance of an Optimized Paper-Based Test for Rapid Visual Measurement of Alanine Aminotransferase (ALT) in Fingerstick and Venipuncture Samples," PLOS One, 10(5): 1-15, May 28, 2015.

Jayawardane et al., "The use of a polymer inclusion membrane in a paper-based sensor for the selective determination of Cu(II)," Analytica Chimica Acta, vol. 803, pp. 106-112, Nov. 25, 2013.

Kaigala et al., "Rapid prototyping of microfluidic devices with a wax printer," Lab Chip, vol. 7, pp. 384-387, Jan. 10, 2007.

Kelly et al., "Thermal Bonding of Polymeric Capillary Electrophoresis Microdevices in Water," Anal. Chem., 75(8): 1941-1945, Apr. 15, 2003.

Khang et al., "Room-temperature imprint lithography by solvent vapor treatment," Applied Physics Letters, 76(7): 870-871, Feb. 4, 2000.

Kho et al., "Aqueous re-dispersibility of spray-dried antibiotic-loaded polycaprolactone nanoparticle aggregates for inhaled antibiofilm therapy," Powder Technology, 203(3): 432-439, Nov. 25, 2010.

Koesdjojo et al., "Fabrication of a Microfluidic System for Capillary Electrophoresis Using a Two-Stage Embossing Technique and Solvent Welding on Poly(methyl methacrylate) with Water as a Sacrificial Layer," Anal. Chem., 80(7): 2311-2318, Apr. 1, 2008.

Koesdjojo et al., "Two-stage polymer embossing of co-planar microfluidic features for microfluidic devices," Sensors and Actuators B, 131(2): 692-697, May 14, 2008.

Kundu et al., "Continuous Flow Enzyme-Catalyzed Polymerization in a Microreactor," JACS, 133(15): 6006-6011, Mar. 25, 2011.

Lai et al., "A Packaging Technique for Polymer Microfluidic Platforms," Anal. Chem., 76(4): 1175-1183, Feb. 15, 2004.

Lee et al., "Microfabricated plastic chips by hot embossing methods and their applications for DNA separation and detection," Sensors and Actuators B, vol. 75, pp. 142-148, 2001.

Lei et al., "Microwave bonding of polymer-based substrates for potential encapsulated micro/nanofluidic device fabrication," Sensors and Actuators A, 114(2-3): 340-346, Feb. 28, 2004.

Li et al., "Polydimethylsioxane Fluidic Interconnects for Microfluidic Systems," IEEE Transactions on Advanced Packaging, 26(3): 242-247, Aug. 2003.

Licata et al., "How to bond polycarbonate parts by solvent welding," Plastics Engineering, 42(6): 53-55, Jun. 1986.

(56) References Cited

OTHER PUBLICATIONS

Lim et al., "Micropatterning and Characterization of Electrospun Poly(ε-Caprolactone)/Gelatin Nanofiber Tissue Scaffolds by Femtosecond Laser Ablation for Tissue Engineering Applications," *Biotechnology and Bioengineering*, 108(1): 116-126, Jan. 1, 2011.
Lin et al., "Low azeotropic solvent for bonding of PMMA microfluidic devices," *Sensors and Actuators B*, 121(2): 698-705, Jun. 2, 2006.
Liu et al., "Fabrication of Balloon-Expandable Self-Lock Drug-Eluting Polycaprolactone Stents Using Micro-Injection Molding and Spray Coating Techniques," *Annals of Biomedical Engineering*, 38(10): 3185-3194, May 22, 2010.
Machell et al., "Optical Properties of Solvent-Cast Polymer Films," *Macromolecules*, 23(1): 186-194, 1990.
Manz et al., "Micromachining of monocrystalline silicon and glass for chemical analysis systems: A look into next century's technology or just a fashionable craze?," *Trends in Analytical Chemistry*, 10(5): 144-149, 1991.
Martinez et al., "Diagnostics for the Developing World: Microfluidic Paper-Based Analytical Devices," *Anal. Chem.*, 82(1): 3-10, Jan. 1, 2010.
McDonald et al., "Fabrication of microfluidic systems in poly(dimethylsiloxane)," *Electrophoresis*, 21(1): 27-40, Jan. 1, 2000.
Muck, Jr. et al., "Fabrication of Poly(methyl methacrylate) Microfluidic Chips by Atmospheric Molding," *Anal. Chem.*, 76(8): 2290-2297, Feb. 28, 2004.
Peeni et al., "Sacrificial layer microfluidic device fabrication methods," *Electrophoresis*, 27(24): 4888-4895, Dec. 2006.
Pengpumkiat et al., "A Paper-Based Disposable Well-Plate for Cyanide Detection Incorporating a Fluorescent Chitosan-CdTe Quantum Dot Nanoparticle," Poster Presentation at PITTCON Conference and Expo 2017, Chicago, Mar. 2017.
Pengpumkiat et al., "A Paper-Based Disposable Well-Plate for Cyanide Detection Incorporating a Fluorescent Chitosan-CdTe Quantum Dot Nanoparticle," Abstract, PITTCON Conference and Expo 2017, Chicago, Mar. 2017.
Rella et al., "Rapid Cyanide Detection Using the Cyantesmo® Kit," *Journal of Toxicology, Clinical Toxicology*, 42(6): 897-900, 2004.
Roberts et al., "UV-Laser Machined Polymer Substrates for the Development of Micro-Diagnostic Systems," *Anal. Chem.*, 69(11): 2035-2042, Jun. 1, 1997.
Rossier et al., "Electrochemical Detection in Polymer Microchannels," *Anal. Chem.*, 71(19): 4294-4299, Oct. 1, 1999.
Rossier et al., "Electrophoresis with electrochemical detection in a polymer microdevice," *Journal of Electroanalytical Chemistry*, 492(1): 15-22, Sep. 29, 2000.
Rossier et al., "Topography, Crystallinity and Wettability of Photoablated PET Surfaces," *Langmuir*, 15(15): 5173-5178, Jun. 25, 1999.
Rundel et al., "Organic solvent nanofiltration for microfluidic purification of poly(amidoamine) dendrimers," *Journal of Chromatography A*, 1162(2): 167-174, Aug. 31, 2007.
Santiago et al., "Peptide-surface modification of poly(caprolactone) with laminin-derived sequences for adipose-derived stem cell applications," *Biomaterials*, 27(15): 2962-2969, Jan. 30, 2006.
Sarasam et al., "Characterization of chitosan-polycapralactone blends for tissue engineering applications," *Biomaterials*, 26(27): 5500-5508, Apr. 7, 2005.
Shah et al., "Capillarity Induced Solvent-Actuated Bonding of Polymeric Microfluidic Device," *Anal. Chem.*, 78(10): 3348-3353, Apr. 12, 2006.
Skotak et al., "Letter to the Editor," *Carbohydrate Polymers*, vol. 5, 1-3, Nov. 5, 2010.
Sousa et al., "Selective Protein Adsorption on a Phase-Separated Solvent-Cast Polymer Blend," *Langmuir*, 22(14): 6286-6292, May 28, 2006.
Sun et al., "Rapid Prototyping of Poly(methyl methacrylate) Microfluidic Systems Using Solvent Imprinting and Bonding," *J. Chromatogr. A*, 1162(2): 162-166, Aug. 31, 2007.
Wang et al., "Towards disposable lab-on-a-chip: Poly(methylmethacrylate) microchip electrophoresis device with electrochemical detection," *Electrophoresis*, 23(4): 596-601, Feb. 4, 2002.
Woodruff et al., "The return of a forgotten polymer—Polycaprolactone in the $21^{st}$ century," *Progress in Polymer Science*, 35(10): 1217-1256, Apr. 7, 2010.
Xie et al., "Gas sensor arrays based on polymer-carbon black to detect organic vapors at low concentration," *Sensors and Actuators B*, 113(2): 887-891, Aug. 24, 2005.
Yang et al., "Microfluidic assisted synthesis of multi-functional polycaprolactone microcapsules: incorporation of CdTe quantum dots, $Fe_3O_4$ superparamagnetic nanoparticles and tamoxifen anticancer drugs," *Lab Chip*, No. 7, pp. 961-965, Dec. 19, 2008.
Ye et al., "DNA separation with low-viscosity sieving matrix on microfabricated polycarbonate microfluidic chips," *Anal. Bioanal. Chem.*, 381(4): 820-827, Jan. 19, 2005.
Yeo et al., "Ultrafast microfluidics using surface acoustic waves," *Biomicrofluidics*, 3(1): 012002-1-012002-23, Jan. 2, 2009.
Ying et al., "Starch/Polycaprolactone Blends Compatibilized with Starch Modified Polyurethane," *Chem. Res. Chinese Universities*, 26(3): 483-487, 2010.
Yokoyama et al., "Detection and Evaluation of Fragrances by Human Reactions Using a Chemical Sensor Based on Adsorbate Detection," *Anal. Chem.*, 65(6): 673-677, Mar. 15, 1993.
Zhang et al., "A paper-based platform for detection of viral RNA," *Analyst.*, 142(5): 815-823, Feb. 27, 2017.
Zhao et al., "Facile preparation of fluorescence-encoded microspheres based on microfluidic system," *Journal of Colloid and Interface Science*, 352(2): 337-342, Dec. 15, 2010.
Zheng et al., "An amperometric biosensor based on hemoglobin immobilized in poly(ε-caprolactone) film and its application," *Biosensors and Bioelectronics*, vol. 23, pp. 1562-1566, Jan. 12, 2008.
Zhou et al., "Poly(ε-caprolactone) as substrate for water denitrification," *Int. J. Environment and Pollution*, 38(3): 349-359, 2009.
Zhu et al., "Surface Modification of Polycaprolactone Membrane via Aminolysis and Biomacromolecule Immobilization for Promoting Cytocompatibility of Human Endothelial Cells," *Biomacromolecules*, 3(6): 1312-1319, Sep. 18, 2002.

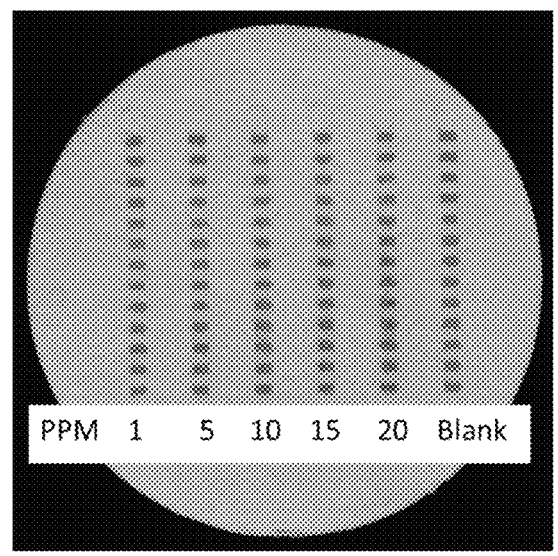
FIG. 1
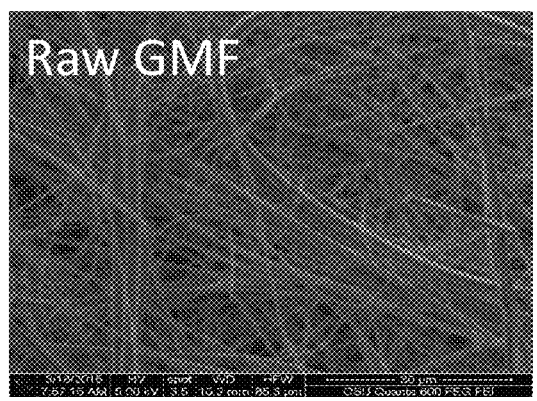 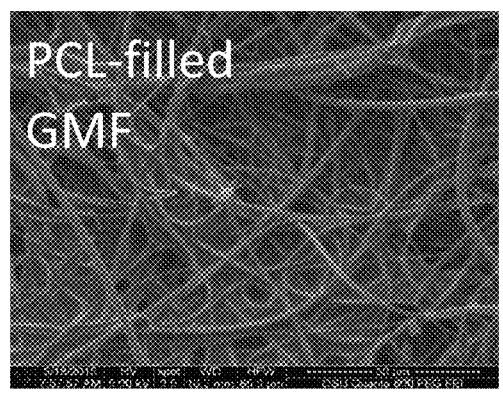
FIG. 2A  FIG. 2B pH 4.0  pH 7.4  pH 9.0

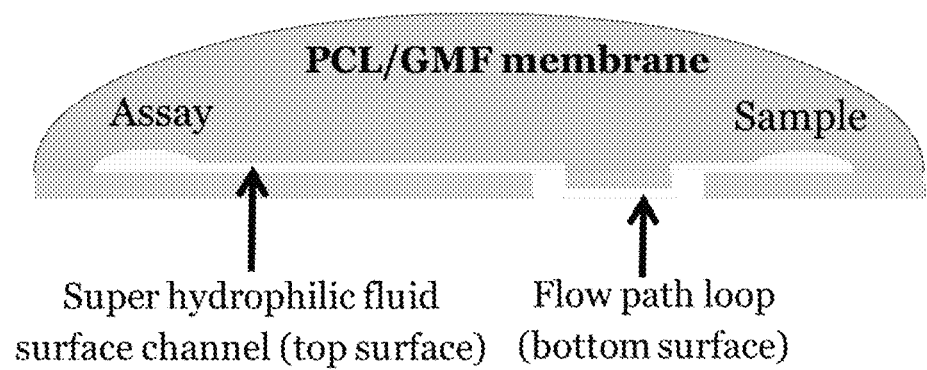
FIG. 14
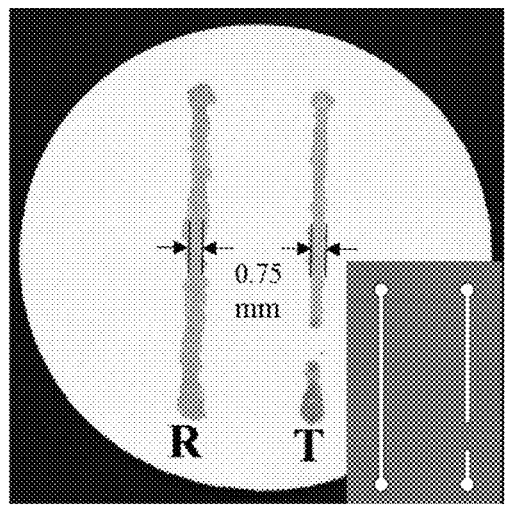 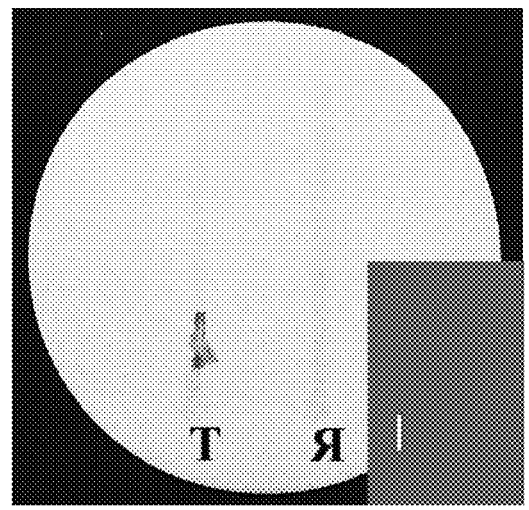
FIG. 15A        FIG. 15B

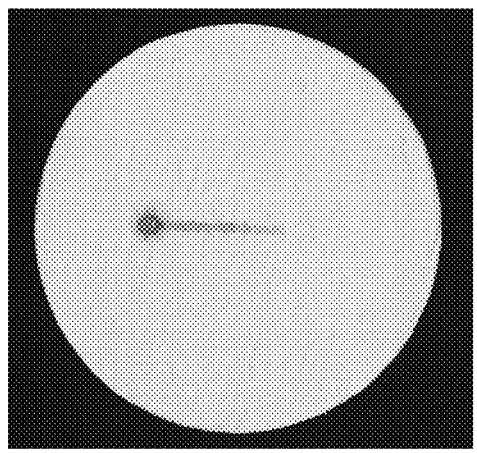
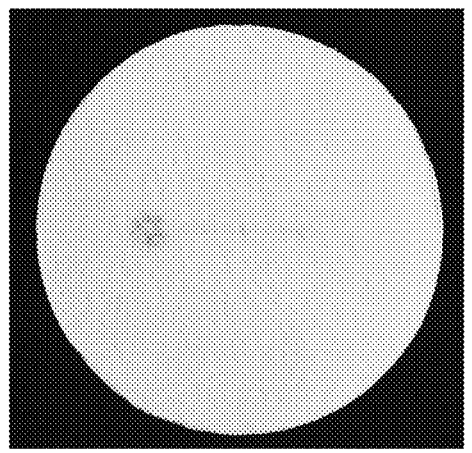
FIG. 17A  FIG. 17B
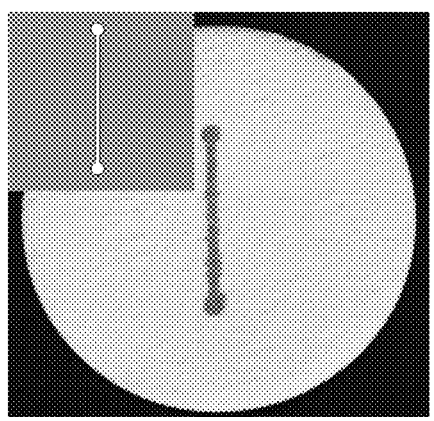
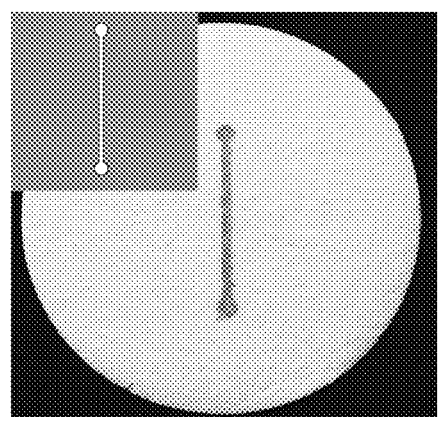
FIG. 18A  FIG. 18B
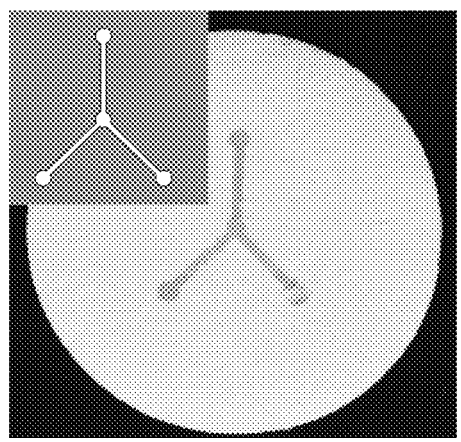
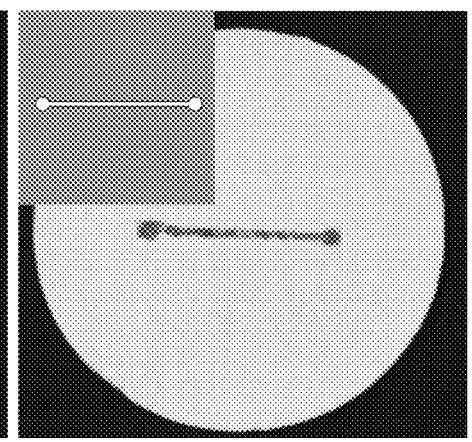
FIG. 19A  FIG. 19B

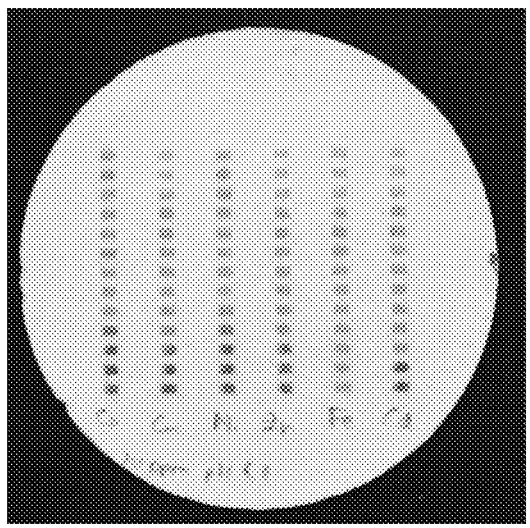 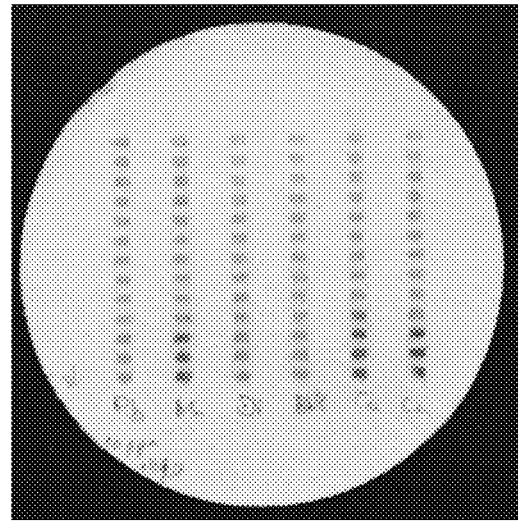
FIG. 20A    FIG. 20B
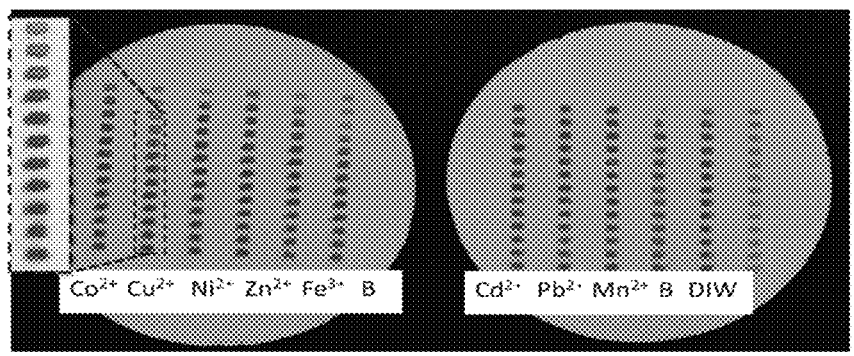
FIG. 20C
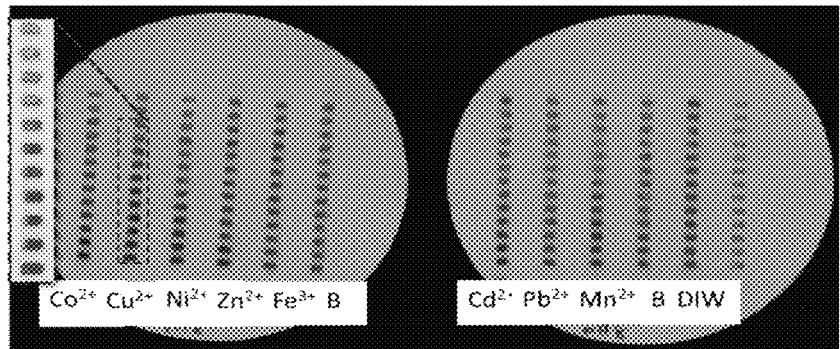
FIG. 20D

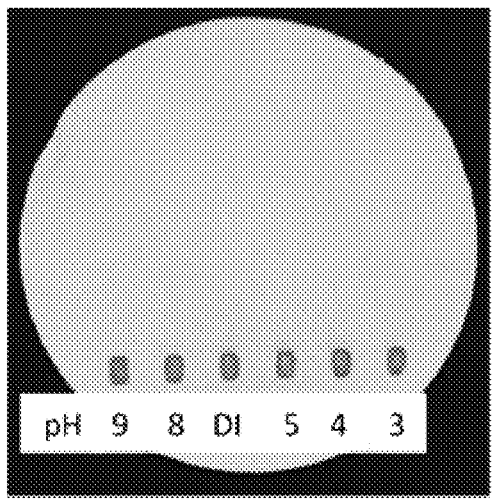 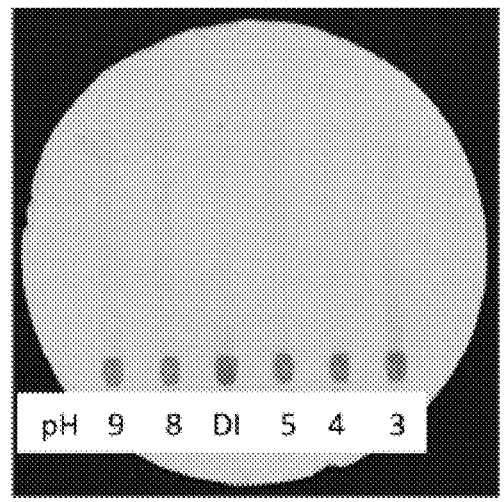
FIG. 23A             FIG. 23B
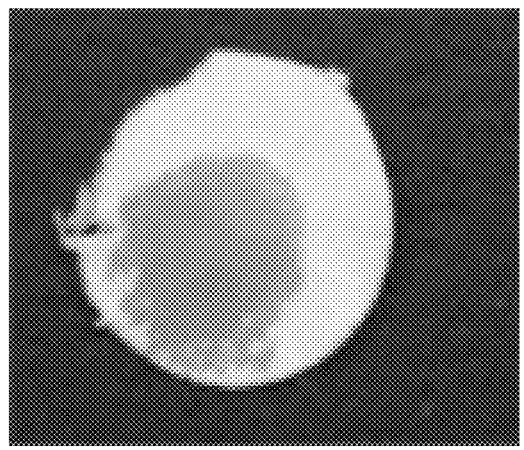 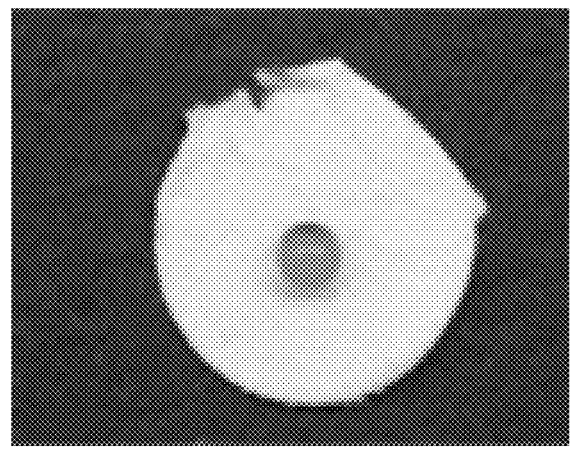
FIG. 24A             FIG. 24B Co²⁺　Cu²⁺　Ni²⁺　Zn²⁺　Fe³⁺　Pb²⁺　Cd²⁺　Mn²⁺

FLUIDIC DEVICES FOR CHROMATOGRAPHIC SEPARATION AND METHODS OF MAKING AND USING THE SAME

CROSS REFERENCE TO RELATED APPLICATION

This application is a continuation of International Application No. PCT/US2017/035018, filed on May 30, 2017, which claims the benefit of the earlier filing date of U.S. Provisional Patent Application No. 62/343,621, filed on May 31, 2016; the entirety of each of these prior applications is incorporated herein by reference.

FIELD

The present disclosure concerns lateral flow and through-flow fluidic devices capable of chromatographic separation, unique methods of making such fluidic devices, as well as methods of using the disclosed fluidic devices.

BACKGROUND

Microfluidic devices have gained much popularity in recent years, as they make possible rapid, inexpensive analytical techniques that can be applied to a wide variety of measurements. The quality of these devices and their range of applicability are highly dependent upon the method of fabrication, materials of manufacture, and the chemistry integrated into them. It is beneficial to have a simple assay chemistry so that devices will be inexpensive, easy to produce, and easy to use. One of the major challenges in adapting a simple chemical assay into a microfluidic format is the elimination of interferences to enable element specific detection. Such processes usually require pre-treatment of sample, highly specific assay chemistries, and/or specific detection mechanisms/instruments, all of which make the process more complicated, expensive, and challenging to adapt to a low-cost microfluidic platform.

Copper is useful heavy metal that is widely used in many modern industrial and technological applications, and also is an essential micronutrient for proper health and development of humans and other animals. However, exposure to high environmental levels of heavy metals, including copper and other micronutrients, especially through drinking water, can lead to toxicity resulting in severe acute and chronic health effects. Regular monitoring of aqueous metal ions, such as copper ions, has become necessary as recent anthropogenic activities have led to elevated environmental concentrations of such metals beyond threshold limits. There exists a need in the art for devices that incorporate a novel, inexpensive, simple, and portable analytical approach to efficiently generate reliable qualitative and quantitative data.

SUMMARY

Disclosed herein are embodiments of fluidic devices that can be used for selective visual detection and separation of analytes in various different samples. In some embodiments, the fluidic devices can comprise a substrate having a first surface and a second surface, an optional polymeric coating that coats or substantially coats the substrate, one or more fluidic channels defined on the first surface of the substrate, the second surface of the substrate, or both, and one or more polymer inclusion membrane spots positioned within the one or more fluidic channels. In yet additional embodiments, the fluidic devices can comprise two or more substrates, wherein each substrate is coated with a polymer inclusion membrane spot and each substrate has a different pH value, and a fluidic channel-containing substrate configured to house the two or more substrates and that comprises a fluidic channel that fluidly connects the two or more substrates. In yet additional embodiments, multidimensional fluidic devices are disclosed that can comprise a substrate that is coated or substantially coated with a polymeric material and that comprises a first surface and a second surface, a flow-through spot formed in the substrate that extends from the first surface to the second surface of the substrate, a fluidic channel formed in second surface of the substrate, and a polymer inclusion membrane spot deposited on the first surface of the substrate near the flow-through spot.

Also disclosed herein are embodiments of methods of making fluidic devices. In some embodiments, the methods can comprise depositing one or more polymer inclusion membrane spots onto a surface of a substrate; placing one or more masks on at least one surface of the substrate to form a masked substrate; fabricating at least one fluidic channel pattern in the one or more masks; exposing the masked substrate to an exposure medium; and removing the one or more masks. In some embodiments, the methods can further comprise coating or substantially coating the substrate with a polymeric material; surface-modifying the substrate by exposing the substrate to a silyl reagent; drying the polymer inclusion membrane composition; creating one or more flow-through spots in the substrate; contacting the fluidic device with a buffer; or any combination thereof.

Also disclosed herein are embodiments of methods of using the disclosed fluidic devices. In some embodiments, the methods involve contacting the fluidic device with a sample by adding the sample to a fluidic channel of the fluidic device. In particular disclosed embodiments, the methods concern identifying and quantifying metal ions present in an aqueous sample.

The foregoing and other objects, features, and advantages of the present disclosure will become more apparent from the following detailed description, which proceeds with reference to the accompanying figures.

BRIEF DESCRIPTION OF THE DRAWINGS

FIG. 1 is a photographic image of an exemplary fluidic device comprising a plurality of polymer inclusion membrane spots configured in a linear pattern.

FIGS. 2A and 2B are SEM images of an uncoated substrate (FIG. 2A) and a polymer-coated substrate (FIG. 2B).

FIGS. 5A and 5B illustrate device embodiments wherein the width of the fluidic channel can be increased so as to accommodate larger concentrations of analytes as compared to narrower fluidic channels, wherein FIG. 5A illustrates the channels prior to sample addition and FIG. 5B illustrates the channels after sample addition.

FIGS. 6A and 6B illustrate device embodiments wherein the number of polymer inclusion membrane spots can be increased in channels of the same width so as to increase detection sensitivity, wherein FIG. 6A illustrates the channels prior to sample addition and FIG. 6B illustrates the channels after sample addition.

FIGS. 7A-7D illustrate device embodiments wherein the width of the fluidic channel can be varied within the channel to provide improved detection limits, wherein FIG. 7A illustrates the channels prior to sample addition; FIG. 7B illustrates the channels after sample addition; FIG. 7C shows a photographic image of an exemplary device prior to sample addition; and FIG. 7D shows a photographic image of an exemplary device after sample addition.

FIG. 14 is an illustration of an exemplary device.

FIGS. 15A and 15B are photographic images of another exemplary device embodiment, with FIG. 15A showing the top of the device and FIG. 15B showing the bottom of the device.

FIGS. 17A and 17B show an exemplary device embodiment that is able to separate hydrophilic samples from hydrophobic samples, wherein a top substrate comprises a fluidic channel through which the hydrophilic sample flows (FIG. 17A), and a bottom substrate comprises a fluidic channel through which the hydrophobic sample flows (FIG. 17B).

FIGS. 18A and 18B are photographic images of an exemplary flow-through device embodiment, with FIG. 18A showing the top of the device and FIG. 18B showing the bottom of the device.

FIGS. 19A and 19B are photographic images of an exemplary lateral surface flow device embodiment, with FIG. 19A showing the top of the device and FIG. 19B showing the bottom of the device.

FIGS. 20A-20D are photographic images of exemplary device embodiments, which illustrate the ability of the device to selectively detect ions using visible chromatographic signals (FIGS. 20A and 20B) as well as by modifying pH (FIGS. 20C and 20D).

FIGS. 23A and 23B are photographic images of a device embodiment showing the sensitivity of the device for ionic species at particular pH values on an unmodified substrate (FIG. 23A) and a TMSCl-treated substrate (FIG. 23B).

FIGS. 24A and 24B are photographic images of an untreated substrate (FIG. 24A) and a TMSCl-treated substrate (FIG. 24B).

FIG. 26A shows how PAN can react with different metal ions to produce different colors; FIG. 26B shows how the disclosed devices can be used to distinguish the presence of different metal ions; and FIG. 26C shows how color signals produced by PAN-$M^{n+}$ complexes can vary with pH.

FIG. 27G is a digital analysis map showing that digital analysis can be used for deconvolution of colorimetric analytical signals.

DETAILED DESCRIPTION

I. Explanation of Terms

Figure 3:
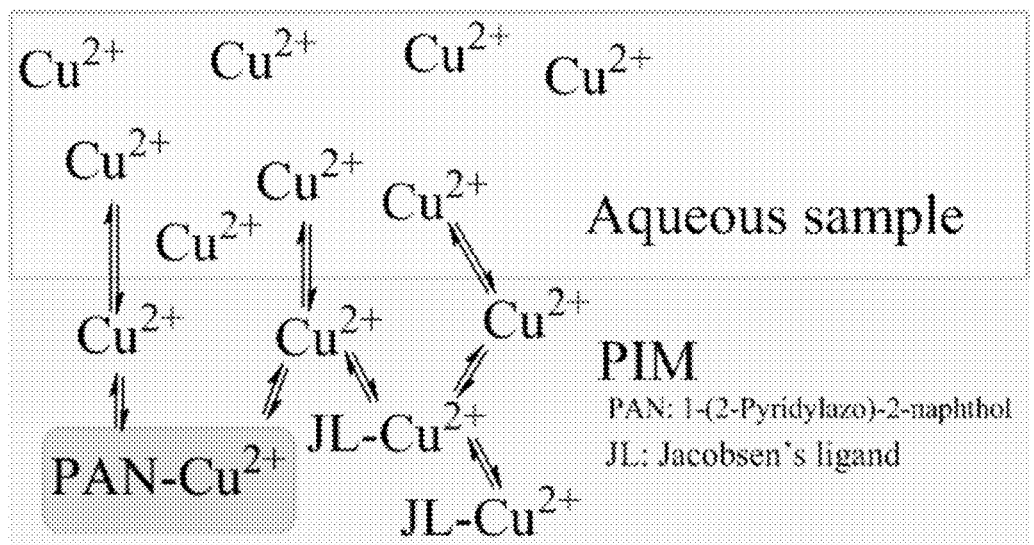
FIG. 3 is a schematic diagram showing the interactions that can occur between ionic species present in an aqueous sample and a representative polymer inclusion membrane comprising a complexation agent (e.g., "PAN") and a transport enhancer component ("JL").

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cylcoalkenyl), cis, or trans (e.g., E or Z).

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

II. Introduction

The quality and range of applicability of conventional fluidic devices (e.g., microfluidic devices) used for analyte qualification and quantification is highly dependent upon the method of fabrication, materials of manufacture, and most importantly the chemistry integrated into them. One of the major challenges in adapting a simple chemical assay into a fluidic (e.g., microfluidic) format is the elimination of interferences to enable element specific detection. Such processes usually require pre-treatment of sample, highly specific assay chemistries, and/or specific detection mechanisms/instruments, all of which make the process more complicated, expensive, and challenging to adapt to the fluidic platform. In contrast to conventional fluidic devices, the present disclosure describes new fluidic devices that utilize a simple assay chemistry, thus making the devices inexpensive, easy to produce, and easy to use.

Heavy metals can be considered one of the most hazardous environmental pollutants. Due to their valuable physical and chemical properties, heavy metals are widely utilized in many modern applications, hence the risk of pollution is very high. One such example is copper, which is used in many areas of application including plumbing for domestic water supplies, as a micronutrient, and in many common valves, fittings, electrical components and machine parts. Exposure to low levels of copper is likely to be beneficial as it is an essential nutrient for proper health and development of humans and animals. However, exposure to higher environmental levels of copper especially through drinking water could lead to the copper toxicity resulting severe health effects such as jaundice, hemoglobinuria, kidney failure, liver damage and potentially death. As a result, the US Environmental Protection Agency (EPA) has published a regulation to control lead and copper in drinking water indicating that copper concentrations should not exceed 1.3 ppm in more than 10% of customer water outlets.

Current analytical techniques for heavy metal analysis require a sophisticated laboratory environment with trained personnel, and expensive instrumentation, such as atomic absorption spectroscopy, atomic emission spectroscopy, and inductively coupled plasma optical emission spectroscopy. Such techniques are suitable for one-time quantitative analysis as they are expensive and time consuming. However, these methods are not practical for constant monitoring or on site applications. Monitoring elevated levels of micronutrient/heavy metal such as copper in drinking/environmental waters requires an inexpensive, rapid and portable analytical tool.

The disclosed lateral flow and flow-through fluidic devices described herein provide a novel and inexpensive fluidic platform that can be used for multiple different purposes, such as environmental analysis, biological analysis, clinical chemistry, medicinal chemistry, water analysis and quality monitoring, industrial process analysis, food and beverage analysis, and the like. The devices provide the ability for a simple chromatographic separation approach on a lateral flow (and/or through-flow) fluidic channel and the ability eliminate interferences for element specific detection using a non-specific assay chemistry.

Also disclosed herein are novel, unique channel fabrication methods that enable making devices comprising a combination of different channel geometries, which can provide highly accurate and sensitive device performance. The disclosed methods minimize environmental impact as little to no toxic chemicals are required and little to no toxic by-products are produced. The methods also maximize biocompatibility as the constructed fluidic devices are useful for analysis of a myriad of analytes and compounds. The disclosed methods of making the devices make it possible to use a non-specific assay to independently detect multiple analytes without any additional chemistry or other instrumental/analytical requirements. In some embodiments, additional analytical components may be added to enhance signal output and processing, further expanding the range of applicable fields. The disclosed methods of making the fluidic devices described herein provide an advantage over the art as conventional flow-based assays using fluidic devices require a particular construction sequence. Conventional methods require that channel and zone fabrication be performed first, followed by dispensation of the assay components. As such, different regions of the fluidic channel are defined through the fabrication process, which requires that the reagents be precisely dispensed subsequent to fabrication. The methods disclosed herein provide the flexibility to define the fluidic channel's shape, placement, and dimensions before or after the application of the assay (e.g., the polymer inclusion membrane component described herein). In the disclosed methods, the shape and dimensions of the fluidic channel can be controlled using a simple masking technique that does not require expensive fabrication instrumentation and that also provides the ability to mask different surfaces of the substrate of the device. As such, rapid prototyping can be implemented. One additional advantage that the disclosed methods provide is the ability to define areas of the assay that the sample can interact with, thereby expanding the effective concentration range of the fluidic device. Channel geometries are thus easily altered even after the assay has been dispensed on the substrate. As such, reactions between analytes in the sample and the assay can be controlled physically as opposed to optimizing reagent concentration and/or other chemical optimization methods.

The devices, methods of making the devices, and methods of using the devices are described in more detail below.

III. Lateral Flow and Flow-Through Fluidic Devices

Disclosed herein are embodiments of fluidic devices that provide chromatographic separation of multiple different analytes using lateral flow and/or flow-through techniques. In particular disclosed embodiments, the devices are microfluidic devices comprising one or more microfluidic channels that provide quantitative and qualitative analysis of chemical analytes, such as ionic species.

In some embodiments, the disclosed fluidic devices comprise a substrate and an assay deposited onto the substrate. In particular disclosed embodiments, the assay can be in the form of a polymer inclusion membrane that is positioned on the substrate in a pattern. An exemplary embodiment of a polymer inclusion membrane patterned on a substrate is shown by FIG. 1.

The substrate can be a hydrophilic substrate, a hydrophobic substrate, a porous substrate, or a combination thereof. In particular disclosed embodiments, porous substrates having sufficient porosity so as to allow penetration of oxygen radicals into the substrate to activate the inner surfaces of the substrate. In some embodiments comprising certain hydrophobic substrates, the substrate need not be further modified with a polymeric coating as described herein for other types of substrates, therefore the polymeric coating can be optional. Some hydrophobic substrates (e.g., substrates comprising Teflon) can be coated with a polymeric coating in some embodiments. The substrates used in the disclosed fluidic devices also are chemically inert and stable and are resistant to heat. In particular disclosed embodiments, the substrate can be a paper substrate (e.g., filter paper such as Whatman 1, Whatman 5, or other substrates), a glass microfiber substrate (Whatman GF/A, GF/B, or other substrates), a polymeric substrate (e.g., such as formed from a thin polymer film having a melting point higher than that of the polymeric material used to coat or substantially coat the substrate), a nylon-based substrate, or a combination thereof. The substrate can have any shape, such as circular, ellipsoidal, square, rectangular, and other geometric shapes. In some embodiments, the substrate can have a thickness ranging from 115 µm to 675 µm, such as 260 µm to 600 µm, or 115 µm to 420 µm. In particular embodiments, the substrate can be a glass microfiber substrate having a thickness ranging from 260 µm to 675 µm, with particular embodiments having a thickness of 260 µm. In particular embodiments, the substrate can be a paper substrate having a thickness ranging from 115 µm to 420 µm, with particular embodiments having a thickness of 180 µm. In some embodiments, the surfaces of the substrate (e.g., top and bottom, or a first and second surface) can be coated or substantially coated with a polymeric material, which is described herein. In particular disclosed embodiments, polymeric material penetrates the surfaces of the substrate and coats (or substantially coats) internal fibers or portions of the substrate located between the two surfaces. In embodiments where the surfaces and/or internal fibers/portions of the substrate are substantially coated, the polymeric material covers greater than 0% to less than 100% of the surface area of each substrate surface and/or internal fibers/portions, such as 50% to 99%, or 60% to 98%, or 70% to 97%, or 80% to 95% of the surface area of each surface and/or internal fibers/portions. In some embodiments, the device can comprise a plurality of substrates.

The polymeric material used to coat the substrate can have a structure satisfying Formula I, illustrated below.

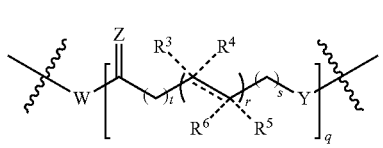

Formula I

With reference to Formula I, Z, Y, and W independently may be selected from O, S, NH, and $NR^2$, where $R^2$ may be selected from hydrogen, aliphatic, aryl, and heteroaryl; each of $R^3$, $R^4$, $R^5$, and $R^6$ (if present) independently may be selected from hydrogen, aliphatic, aryl, heteroaryl, and a heteroatom-containing moiety selected from halogen (e.g. F, Cl, Br, and I), aldehyde (—$R^a$CHO), acyl halide (—$R^a$C(O)X) (where X is selected from fluorine, chlorine, bromine, and iodine), carbonate (—$R^a$OC(O)O$R^b$), carboxyl (—$R^a$C(O)OH), carboxylate (—$R^a$COO$^-$), ether (—$R^a$O$R^b$), ester (—$R^a$C(O)O$R^b$, or —$R^a$OC(O)$R^b$), hydroxyl (—$R^a$OH), ketone (—$R^a$C(O)$R^b$), silyl ether ($R^b R^c R^d$SiO$R^a$—), peroxy (—$R^a$OO$R^b$), hydroperoxy (—$R^a$OOH), phosphate (—$R^a$OP(O)(OH)$_2$), phosphoryl (—$R^a$P(O)(OH)$_2$), phosphine (—P$R^a R^b R^c$), thiol (—$R^a$SH), thioether/sulfide (—$R^a$S$R^b$), disulfide (—$R^a$SS$R^b$), sulfinyl (—RaS(O)$R^b$), sulfonyl (—RaSO$_2$R$^b$), carbonothioyl (—R$^a$C(S)R$^b$ or —R$^a$C(S)H), sulfino (—R$^a$S(O)OH), sulfo (—R$^a$SO$_3$H), thiocyanate (—R$^a$SCN), isothiocyanate (—R$^a$NCS), oxazole, oxadiazole, imidazole, triazole, tetrazole, amide (—R$^a$C(O)NR$^b$R$^c$, or —R$^a$NR$^b$C(O)R$^c$), azide (N$_3$), azo (—R$^a$NNR$^b$), cyano (—R$^a$OCN), isocyanate (—R$^a$NCO), imide (—R$^a$C(O)NR$^b$C(O)R$^c$), nitrile (—R$^a$CN), isonitrile (—R$^a$N$^+$C$^-$), nitro (—R$^a$NO$_2$), nitroso (—R$^a$NO), nitromethyl (—R$^a$CH$_2$NO$_2$), and amine (—R$^a$NH$_2$, —R$^a$NHR$^b$, —R$^a$NR$^b$R$^c$), wherein R$^a$ can be selected from a bond, aliphatic, aryl, heteroaliphatic, or heteroaryl; and each R$^b$, R$^c$, and R$^d$ independently is selected from hydrogen, aliphatic, aryl, heteroaliphatic, heteroaryl, and any combination thereof. In particular disclosed embodiments, Formula I may comprise one or more conjugated or unconjugated olefins. In embodiments where Formula I comprises one or more conjugated or unconjugated olefins, only one of R$^3$ and R$^4$ and only one of R$^5$ and R$^6$ is present in Formula I. In embodiments where Formula I does not comprise one or more conjugated or unconjugated olefins, all of R$^3$, R$^4$, R$^5$, and R$^6$ may be present in Formula I. In particular disclosed embodiments, r may range from 1 to 4, more typically from 1 to 3; even more typically from 1 or 2; s and t independently may range from 0 to about 4 or 0 to 3, or 0 to 2, or 0 to 1; more typically s and t range from 1 to 4, or 1 to 3, or 1 to 2. In particular disclosed embodiments, q ranges from at least 1 to about 1000, or at least 1 to about 900, or at least 1 to about 800, or at least 1 to about 700, or at least 1 to about 600, or at least 1 to about 500, or at least 1 to about 300, or at least 1 to about 250, or at least 1 to about 200, or at least 1 to about 150, or at least 1 to about 100.

In particular disclosed embodiments, the polymeric material used to coat the substrate has a Formula II, III, or IV, each of which is illustrated below. Each of W, Z, Y, R$^3$, R$^4$, R$^5$, R$^6$, q, and r can be as recited above.

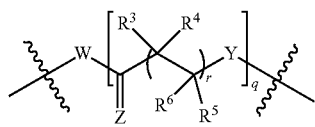

Formula II

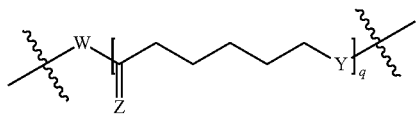

Formula III

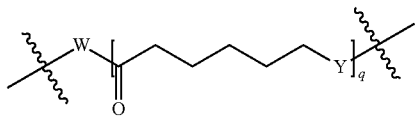

Formula IV

In particular embodiments, the polymeric material may be selected from the following exemplary compounds: polycaprolactone, polycaprolactone diol, polycaprolactone triol, polycaprolactone-block-polytetrahydrofuan-block poly-caprolactone, poly(ethylene oxide)-block-polycaprolactone, poly(ethylene glycol)-block-poly(e-caprolactone) methyl ether, and combinations thereof. In particular disclosed embodiments, the polymer can be any other suitable polymer having ester or epoxy groups, such as polylactic acid or polyvinyl chloride, or an epoxy-based polymer, such as SU-8.

Particular disclosed working embodiments concern using polycaprolactone as a polymeric material, the structure for which is shown below (wherein q is as recited herein). In particular disclosed embodiments, the polycaprolactone has a molecular weight ranging from 500 g/mol to at least 100,000 g/mol; more typically from 10,000 g/mol to 14,000 g/mol; more typically from 70,000 g/mol to 90,000 g/mol. Any polycaprolactone compounds or derivatives thereof having any molecular weight falling within the disclosed ranges are contemplated by the present disclosure. In exemplary embodiments, the polymeric material is polycaprolactone having a molecular weight of 25,000 g/mol.

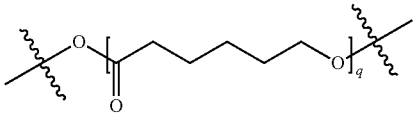

Polycaprolactone

The substrate can be modified to comprise at least one fluidic channel, such as a microfluidic channel. In particular disclosed embodiments, the fluidic channel begins at one point and terminates at one or more points. In some embodiments, the fluidic channel can further comprise one or more sample pre-treatment regions and/or flow-through sections that can be configured to accept a buffer solution, such as would be used to modify the pH of the sample introduced to the fluidic channel as discussed herein, or a polymer inclusion membrane. The fluidic channel can be formed on one or more surfaces of the substrate. In embodiments where the fluidic channel is formed on one surface of the substrate, lateral flow can be used to evaluate the presence (or absence) of analytes in the sample. In embodiments where fluidic channels are formed on two different surfaces of the substrate (e.g., a top and bottom surface, or a first and second surface), flow through the substrate can be used to evaluate the presence (or absence) of analytes in the sample. The dimensions of the fluidic channel can be modified so as to accommodate different concentrations of the analyte(s) in the sample being analyzed. In some embodiments, wider channels can accommodate higher concentrations (e.g., 10 ppm to 50 ppm or higher, such as 10 ppm to 40 ppm, or 10 ppm to 30 ppm, or 10 ppm to 20 ppm) of the analyte(s) and narrower channels can be used to evaluate samples having lower concentrations (e.g., less than 1 ppm to 10 ppm, such as 0.1 ppm to 10 ppm, or 0.5 ppm to 10 ppm) of the analyte(s). In some embodiments, the fluidic channel can have dimensions as follows: widths ranging from 0.05 mm to 1 cm or higher, such as 0.5 mm to 2 mm, or 0.75 mm to 1.25 mm, and lengths ranging from greater than 0 mm to 10 mm or higher, such as greater than 0 mm to 5 mm. In some embodiments, fluid flow occurs on the surface of the substrate and thus need not penetrate into the substrate. In other embodiments, such as flow-through device embodiments, the fluidic channel can have a depth that penetrates through the top (or first) surface of the substrate through to the bottom (or second) surface of the substrate. In some embodiments, a plurality of fluidic channels are patterned onto one or more surfaces of the substrate. The plurality of fluidic channels can be arranged in parallel or in any other desired geometrical arrangement.

In additional embodiments, one or more of the surfaces of the substrate can be surface-modified so as to prevent undesired interactions between the analyte(s) and chemical moieties making up the surfaces of the substrate. Even if the substrate is coated with the polymeric material, it is still possible that such undesirable interactions can occur. For example, SEM images of an uncoated substrate and a PCL-coated substrate are shown in FIGS. 2A and 2B, respectively. As can be seen in FIG. 2B, there is still a considerable amount of the substrate that comprises silanol groups, even after being exposed to the polymeric material. In such embodiments, the substrates can comprise surface chemistries having free hydroxyl groups that may interact with ionic analytes, which can prevent analyte transport with the fluid flow. For example, glass microfiber substrates can comprise such surface chemistries. Accordingly, the hydroxyl groups can be converted to functional groups that do not interact with the ionic analytes in a manner that prevents or disrupts flow. In some embodiments, one or more surfaces of the substrates is exposed to a reagent having a functional group that can interact with the oxygen atom of the hydroxyl group. In particular disclosed embodiments, one or more surfaces of the substrate is exposed to a silyl reagent, such as a chlorosilane (e.g., trimethylsilyl chloride (TMSCl), dimethyl t-butyl silyl chloride (TBSCl), triethylsilyl chloride (TESCl), tributylchlorosilane, or dimethyldichloro silane or the like); aminosilanes (e.g., (dimethylamino)trimethylsilane, or bis(dimethylamino)dimethylsilane); iodo silanes (e.g., iodotrimethylsilane); silazanes (e.g., hexamethyldisilazane); or aminoproppyltriethoxysilane. The silyl reagents react with the free hydroxyl group so as to convert it to a silyl-protected moiety that does not interact with ionic species. An exemplary reaction scheme, Scheme 1, is provided below and showing a particular embodiment of surface modification.

Scheme 1

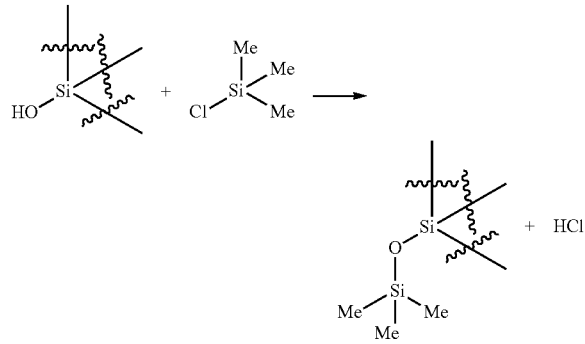

In some embodiments, surface modification also can be done by changing the pH of the sample that is added to the fluidic device for analysis. In such embodiments, if the pH is lowered (e.g., from pH 6.0 to pH 4.0), the concentration of H⁺ will increase and can thereby react with the functional groups found on the surface of the substrate (or within the substrate). In some embodiments, the increased concentration of H⁺ can interact with negatively charged, or neutral, silanol groups found on the surface of (or within) the substrate. In such embodiments, ions present in the sample are free to interact with a complexation agent of the polymer inclusion membrane. In an independent embodiment, the substrate is free of, or does not comprise, a wax coating or other component comprising wax.

The fluidic devices described herein further comprise an assay deposited onto the substrate that is used to detect the presence, or absence of analytes in a sample. In some embodiments, the assay is in the form of a polymer inclusion membrane, which typically is deposited as spots on one or more surfaces of the substrate in a particular pattern. In particular disclosed embodiments, the polymer inclusion membrane is deposited onto a polymer-coated substrate. The polymer inclusion membrane is formed using a composition comprising a polymeric material and a complexation agent. In particular disclosed embodiments, the polymeric material can have a formula according to any one of Formulas I-IV described herein. In exemplary embodiments, the polymeric material is polycaprolactone. The complexation agent can be a ligand configured to form a complex with one or more ionic species. In some embodiments, the complexation agent can be an agent or ligand that is insoluble in water, colored or colorless in a native state, and forms colored complexes with ionic species, which may be water soluble or water insoluble. In yet additional embodiments, the complexation agent can be an agent or ligand that is soluble in water, is colorless in a native state, and forms colored complexes with ionic species. In some embodiments, the complexation agent is a ligand capable of forming a metal-coordination complex with a metal ion. In some embodiments, the complexation agent can be a ligand selected from 1-(2-pyridylazo)-2-naphthol (also referred to herein as PAN), 1-(2-thiazolylazo)-2-naphthol, 2-(2-pyridylazo)-1-naphthol, 4-(2-pyridylazo)-1-naphthol, 4-(5OChloro-2-pyridylazo)-1,3-diaminobenzene, 4-(2-pyridylazo)resorcinol, or 4-(2-thiazolylazo)resorcinol, 2-(2-thiazolylazo)-5-dimethylaminophenol, glyoxal bis(2-hydroxyanil), o-salicylidene-aminophenol, 3-hydroxypicolinaldehyde azine, chloranilic acid, N-benzoyl-N-phenlhydroxylamine, poly(macrocyclic) compounds, o,o-dihydroxyarylazo compounds, azoazoxy BN, dimethylglyoxime, tiron, catechol, or porphyrin compounds. In an independent embodiment, the complexation agent is not or is other than dimethylglyoxime. The amount of the complexation agent used in the polymer inclusion membrane can be an amount that provides a 1:2 (ion:complexation agent) stoichiometry. In particular disclosed embodiments, the amount of the complexation agent ranges from 1 mg/L to 5 g/L, such as 100 mg/L to 1 g/L, or 500 mg/L to 750 mg/L, with particular embodiments utilizing 500 mg/L.

In some embodiments, the composition can further comprise a transport enhancer component that facilitates transfer of ionic species from the sample being analyzed into the deposited polymer inclusion membrane. If a transport enhancer component is used in the composition used to make the polymer inclusion membrane, it can be selected from a compound comprising functional groups capable of coordinating one or more ionic species (e.g., metal ions) so as to promote transfer of the ionic species from an aqueous sample to the polymer inclusion membrane. The transfer enhancer component can be a compound comprising one or more heteroatom-containing functional groups capable of coordinating with a metal ion, such as an oxygen-containing, phosphorous-containing, nitrogen-containing, or sulfur-containing functional groups. In particular disclosed embodiments, the transfer enhancer component is a ligand that does not produce a colored complex upon coordination with an ionic compound, insoluble in water, and has a complex formation constant (or affinity for the ionic species) that is different from the complexation agent. In particular disclosed embodiments, the compound is (R,R)—(−)—N,N'-Bis(3,5-di-tert-butylsalicylidene)-1,2-cyclohexanediamine (referred to herein as Jacobsen's ligand), salen ligands, acac ligands, nitrilotriacetic acid, cation exchange resin compounds, bipyridine, 1,3-diphenylguanidine, diantipyrylmethane, immobilized ethylenediaminetetraacetic acid, and derivatives thereof. The transfer enhancer can be present in an amount ranging from 1000 mg/L to 20 g/L, such as 1000 mg/mL to 15 g/L, with particular embodiments using 4 g/L.

In yet additional embodiments, the composition can further comprise a plasticizer. The plasticizer can be used to modify the elasticity of the polymer inclusion membrane deposited on the substrate. Any suitable plasticizer can be used, with exemplary embodiments being (but not limited to) bis(2-ethylhexyl) sebacate, bis(2-ethylhexyl) phthalate, diisooctyl phthalate, or combinations thereof. Additionally, the composition can comprise a suitable solvent, such as hydrocarbon-based solvents like toluene, xylenes, benzene, and the like.

In particular disclosed embodiments, the active colorimetric complexation agent used in the polymer inclusion membrane is PAN. PAN is an organic ligand that forms different colored complexes with various common heavy metal ions (e.g., complexes having a formula PAN-$M^{n+}$, wherein M is a metal and n is 1, 2, 3, or 4, or so on). In some embodiments, $Cu^{2+}$ can react with PAN in 1:1 stoichiometry to form a red colored copper-PAN ligand complex. Even though most PAN-$M^{n+}$ complexes are precipitates and insoluble in water, the PAN-$Cu^{2+}$ complex is soluble in water at neutral pH or lower (e.g., pH below 5). Thus, in some embodiments, these complexes can be formed on the disclosed devices thereby separating PAN-$Cu^{2+}$ complexes from the organic polymer inclusion membrane, providing the ability to specifically detect $Cu^{2+}$ in an aqueous sample. As the polymer inclusion membrane is organic in nature and PAN in immobilized in it, the $Cu^{2+}$ ions in the aqueous sample must be able to transfer into the polymer inclusion membrane to form PAN-$Cu^{2+}$ complex. Therefore, the $Cu^{2+}_{(sample)} \leftrightarrow Cu^{2+}_{(polymer\ inclusion\ membrane)}$ equilibrium should lean towards the right to achieve a suitable analytical signal. The rate of the equilibrium can determine the time of analysis. A transfer enhancer component (e.g., Jacobsen ligand) can be used to coordinate metals through functional groups present on the transfer enhancer component (e.g., imine nitrogen and hydroxyl groups of the Jacobsen ligand). Therefore, more copper ions can be transferred into the polymer inclusion membrane and thereby indirectly promote the PAN-$Cu^{2+}$ equilibrium (FIG. 3).

IV. Methods of Making Lateral Flow Fluidic Devices

Disclosed herein are embodiments of making the fluidic devices of the present disclosure. In particular disclosed embodiments, the methods can comprise depositing one or more spots of a polymer inclusion membrane composition onto a substrate; placing one or more masks on a surface of the substrate to form a masked substrate; fabricating at least one fluidic channel pattern in the one or more masks; exposing the masked substrate to an exposure medium; and removing the one or more masks to provide the fluidic device.

Figure 4:
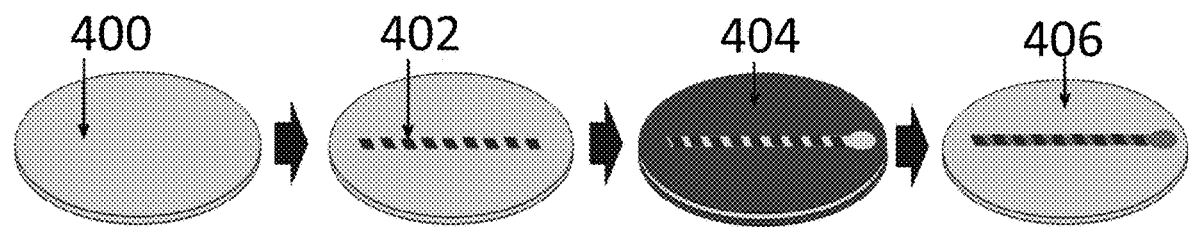
FIG. 4 is a schematic diagram illustrating a representative method for making a fluidic device as disclosed herein.

An exemplary method embodiment is illustrated in FIG. 4, which illustrates exemplary fabrication steps used to make a representative device. With reference to FIG. 4, a polymer filled/coated substrate (e.g., a PCL-filled/coated glass microfiber substrate) (400) is provided. A polymer inclusion membrane composition is dispensed on the substrate and allowed to dry to form the polymer inclusion membrane (402). A representative pattern of the polymer inclusion membrane is illustrated in FIG. 4, but other patterns also are contemplated. Also, as illustrated in FIG. 4, a mask is applied to both surfaces of the substrate, with the mask applied to the top surface comprising the desired microfluidic pattern (404). After oxygen radical exposure, the masks are removed to reveal the defined microfluidic assay device (406).

In particular disclosed embodiments, the one or more spots of the polymer inclusion membrane composition can be deposited on the substrate in a pattern having any desired shape or configuration (e.g., circular, rectangular, oval, linear, in parallel, and the like). The spots can be deposited as spherical spots, square spots, rectangular spots, ellipsoidal spots, or any other suitable shape. In some embodiments, the deposited spot can have an area ranging from 10 $\mu m^2$ to 2 $cm^2$, such as 100 $\mu m^2$ to 2000 $\mu m^2$, or 250 $\mu m^2$ to 1500 $\mu m^2$. In some embodiments, the volume of the deposited spots is determined by the fluidic channel width to be used for the device. Solely by way of example, in device embodiments comprising a fluidic channel having a width of 0.75 mm, the polymer inclusion membrane spots can have a volume that provides a polymer inclusion membrane spot having dimensions of 0.5 mm and 1 mm, such as 25 nL of the polymer inclusion membrane composition. In this example, analyte concentrations ranging from 0 ppm to 10 ppm can be detected. In yet additional embodiments, multiple applications of the polymer membrane composition can be used to provide polymer inclusion membrane spots having the ability to detect larger concentrations of analytes (e.g., 0 ppm to greater than 10 ppm, such as 0 ppm to 20 ppm). In some embodiments, the volume of the polymer inclusion membrane spot can range from 1 nL to 25 µL per spot. The polymer inclusion membrane composition also can be added to the substrate so as to coat or substantially coat the substrate.

In some embodiments, the method can further comprise treating the substrate with a polymeric material to form a coated, or substantially coated substrate. In such embodiments, the substrate typically is coated or substantially coated with the polymeric material before the polymer inclusion membrane composition is deposited. The substrate can be coated or substantially coated with the polymeric material by dipping the substrate in the polymeric material, spraying the substrate with the polymeric material, spin-coating the substrate with the polymeric material, or other suitable coating methods. In yet additional embodiments, the method can further comprise surface-modifying the substrate prior to or after the substrate is coated with the polymeric material.

Figure 5A:
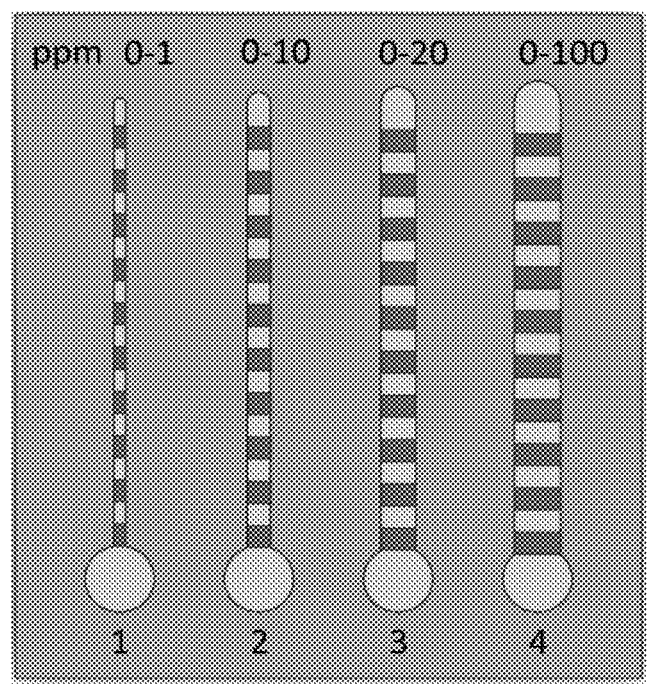
Figure 5B:
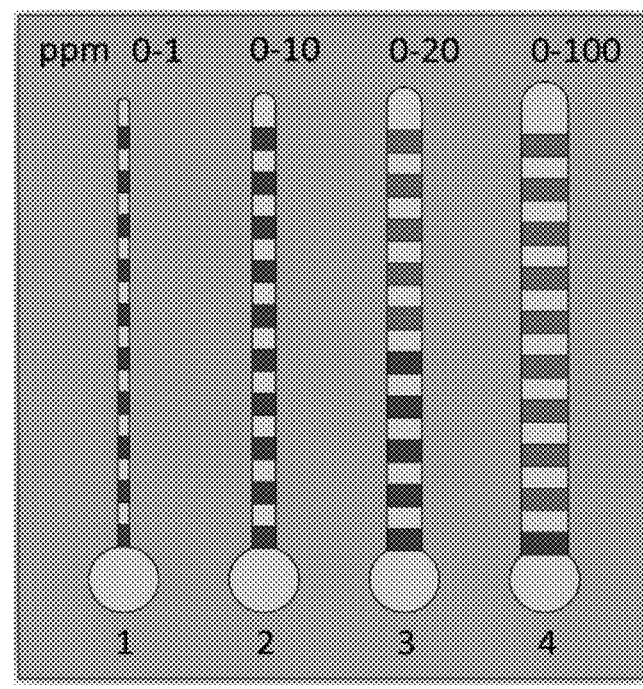

The polymer inclusion membrane can be deposited by hand or with an instrument, such as a pipette, ink-jet printer, or the like. Once the polymer inclusion membrane composition is deposited, the method can further comprise a drying step whereby the polymer inclusion membrane composition is dried so as to the polymer inclusion membrane. This can comprise an affirmative drying step (e.g., heating or passing an inert gas over the composition), or simply can involve allowing the solvent in the polymer inclusion membrane to evaporate naturally. The amount of the polymer inclusion membrane composition that is deposited on the substrate can be tuned to accommodate different sample concentrations. For example, a larger spot of the polymer inclusion membrane composition can be deposited so that a higher concentration of analytes can interact with the polymer inclusion membrane formed therefrom. In other embodiments, smaller spots of the polymer inclusion membrane composition can be deposited so that a lower concentration of analytes can interact with the polymer inclusion membrane formed therefrom. In some embodiments, a combination of large and small spots can be used. Also, the number of spots of deposited polymer inclusion membrane can be modified so as to increase the resolution of the chromatographic signal produced by the assay. FIGS. 5A and 5B illustrate an exemplary embodiment whereby the size of the polymer inclusion spots can be increased so as accommodate testing different concentrations of analytes. FIG. 5A illustrates four different fluidic channels having different and increasing widths (channel $1_w$<channel $2_w$<channel $3_w$<channel $4_w$, wherein w=width) with the same number of polymer inclusion spots before a sample is added. FIG. 5B shows the fluidic channels after the sample is added to the fluidic channels, where channel 1 can detect concentrations from 0-1 ppm, channel 2 can detect concentrations from 0-10 ppm, channel 3 can detect concentrations from 0-20 ppm, and channel 4 can detect concentrations from 0-100 ppm. As the area of the polymer inclusion membrane spots increase, sample capacity (loading capacity) likewise increases. The distance between each polymer inclusion membrane spots can be adjusted based on the level of detection desired. For example, high precision embodiments can have distances ranging from 5 nm to 250 µm, such as 10 nm to 100 µm, or 50 nm to 500 nm, or 100 nm to 250 nm. Also by example, visual detection embodiments (that is, embodiments where the presence (or absence) of analytes is assessed by the naked eye) can utilize distances ranging from 250 µm to 2 mm or higher, such as 250 µm to 1 mm, or 500 µm to 750 µm.

Figure 6A:
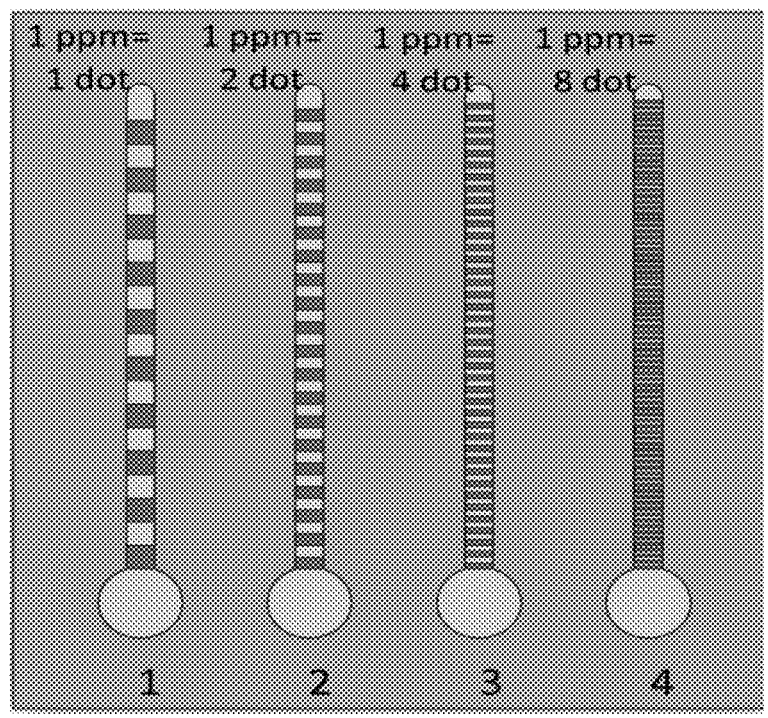
Figure 6B:
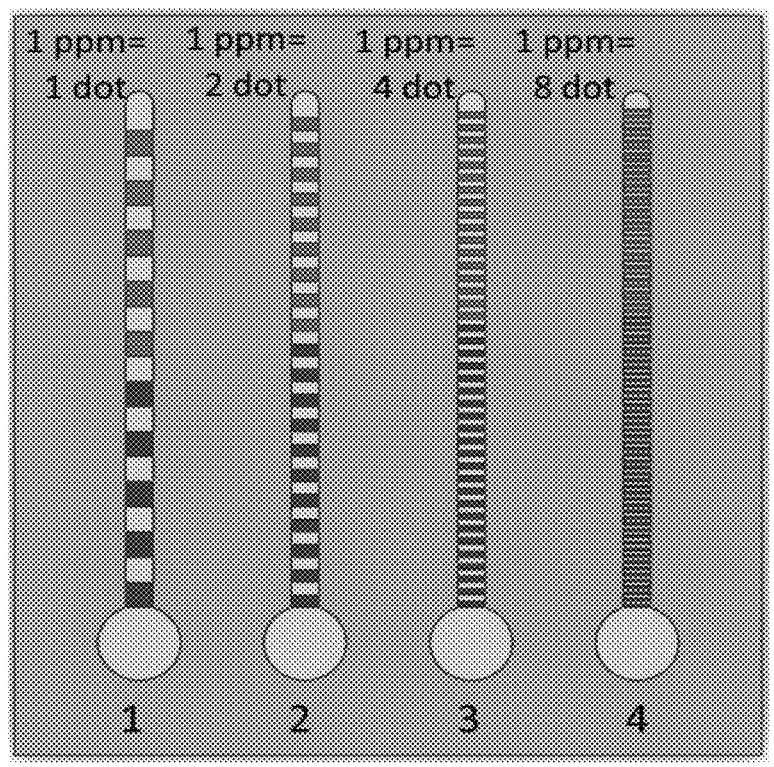

In some embodiments of using the method, the number of spots can represent a unit concentration. Thus, in some embodiments, the accuracy of the methods can be increased by increasing the number of spots of the polymer inclusion membrane deposited on the substrate. To provide a high number of spots with good accuracy, a high precision deposition tool, such as an ink jet printer can be used. An illustration of fluidic channels of a device having increased spot deposition and accuracy can be seen in FIGS. 6A and 6B. With reference to FIG. 6A, each spot in channel 1 corresponds to an analyte concentration of 1 ppm, whereas two spots in channel 2 corresponds to an analyte concentration of 1 ppm, four spots in channel 3 corresponds to an analyte concentration of 1 ppm, and eight spots in channel 4 corresponds to an analyte concentration of 1 ppm. Thus, as the number of spots per ppm is increased, the sensitivity of concentration determination can be improved. For example and with reference to FIG. 6B, the sensitivity increase can be seen by comparing channel 1 after the sample is added, where the concentration is 5 ppm, with channel 4 after the sample is added, where the concentration is 5.875.

In some embodiments, the method comprises masking the substrate with one or more masks. Such masks can be made from an inexpensive tape (or any similar suitable material), and are used to cover the area on the substrate that comprises the polymer inclusion membrane dispensed area on the polymer-filled membranes. In yet additional embodiments, the masks are not adhesive and a separate adhesive is used to adhere it to the substrate. The masks can be attached to a surface of the substrate, such as the top surface or the top and bottom surfaces of the mask (or a first and/or second surface of the substrate). The mask can cover or substantially cover the substrate, including the deposited polymer inclusion membrane. In some embodiments, the mask can be prefabricated with a fluidic channel pattern before it is attached to the substrate, or the mask can be attached to the substrate and the fluidic channel pattern fabricated in the mask while attached to the substrate. In some embodiments, only one mask comprises the fluidic channel pattern (such as the mask on the top, or first, surface of the substrate). In other embodiments, both masks can comprise a fluidic channel pattern. In embodiments where only the mask on the top surface contains a fluidic channel pattern, fluid flow occurs only on that surface, significantly reducing sample/reagent consumption. In embodiments where two masks are attached to both a top and bottom (or first and second) substrate and the two mask have the same or substantially the same fluidic channel pattern, the addition of a sample onto one surface also wets the other surface of the substrate, which can allow for larger sample volumes to be evaluated.

Figure 7A:
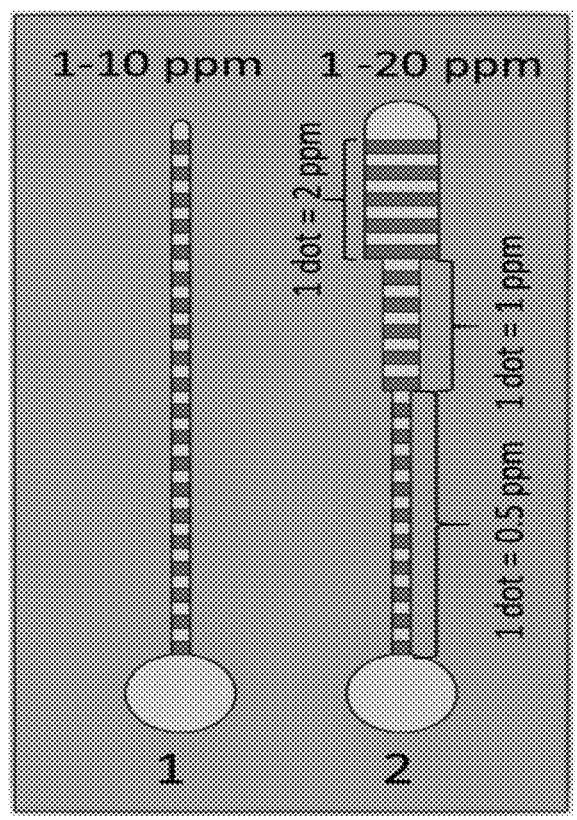
Figure 7B:
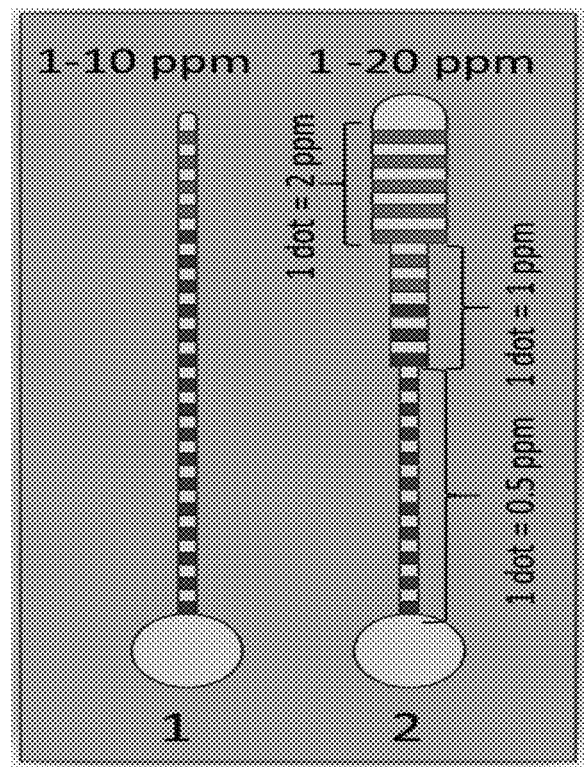
Figure 7C:
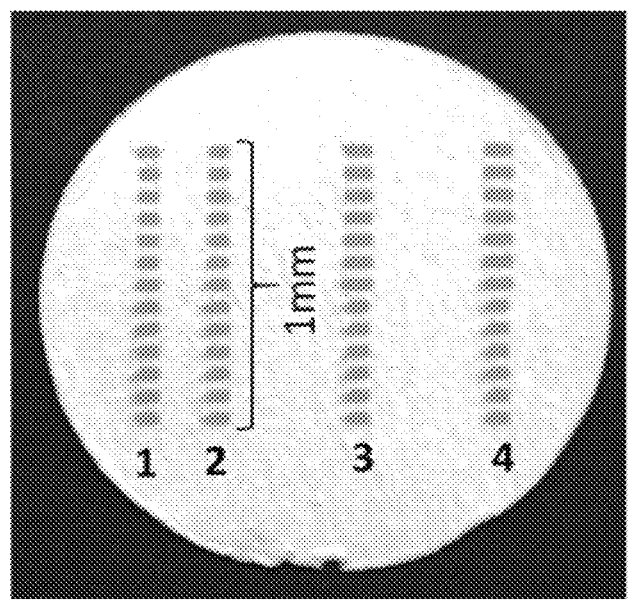
Figure 7D:
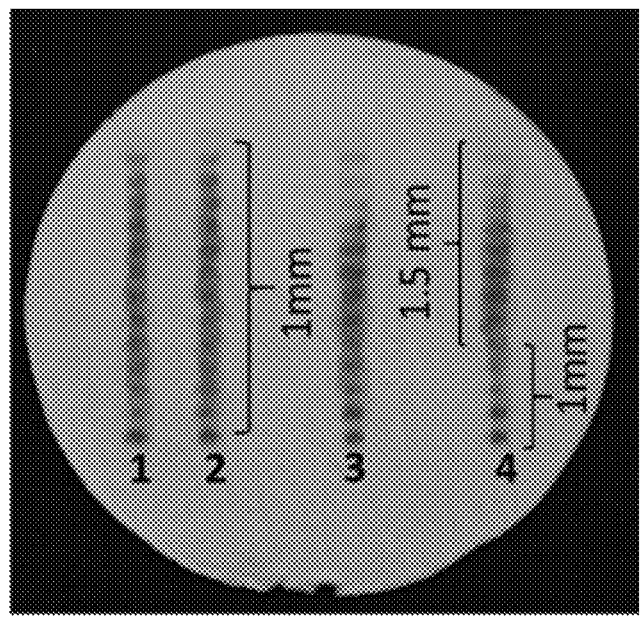

As indicated above, the fluidic channel pattern can be fabricated in a mask before or after it has been attached to the substrate. In some embodiments, the fluidic channel can be fabricated so as to physically accommodate the dispensed polymer inclusion membrane, or to physically define a particular portion of the deposited polymer inclusion membrane to be used for analysis. The microfluidic pattern is created by cutting the desired pattern/geometry into the mask using a suitable cutting tool (e.g., a laser cutter, cutting plotter, film cutter, and the like) prior to or after assembly. In some embodiments, both masks can be configured to have one or more fluidic channels wherein the fluidic channel fabricated on each mask is the same or different geometry, thus providing multidimensional fluidic devices. In yet additional embodiments, both masks can have the same or different number of fluidic channels. In particular disclosed embodiments, the mask has an adhesive property, which provides facile cutting of the microfluidic pattern into the mask even when the mask is on the substrate. The dimensions of the fluidic channel(s) formed in the mask can be modified so as to limit the amount of reagent exposure on a single polymer inclusion membrane spot. Solely by way of example, an available assay area is lower on a fluidic channel having a narrow width as compared to a larger assay area in a fluidic channel having a wider width because the spot size of the polymer inclusion membrane is limited by the edges of the fluidic channel. In some embodiments, if the analyte concentration is low, it will produce a more readily distinguishable signal on a narrow fluidic channel than on a wide channel (e.g., channel 1 on FIGS. 5A and 5B) since the analyte travels further on the narrow channel before it is fully consumed. Similarly, if the analyte concentration is high, the sample quickly saturates narrow channels but produces a good signal on wider channels (e.g., channel 3 on FIGS. 5A and 5B). In additional embodiments, the dimensions of a single fluidic channel can be modified to include a narrow section, an intermediate section, and a wide section. An exemplary embodiment of such a device is illustrated in FIGS. 7A-7D. With reference to FIG. 7A, two fluidic channels are fabricated in the substrate, one channel having a single width (channel 1) and the other having a variety of widths (channel 2). Changing the width of the fluidic channel allows for detection of higher analyte concentrations (FIG. 7B) increasing the usable range while maintaining the accuracy of the measurement at low concentrations. FIGS. 7C and 7D show actual device embodiments before (FIG. 7C) and after (FIG. 7D) exposure to a sample.

Once the fluidic pattern is cut into the mask, an exposure step can be performed to fix the pattern from the mask onto the substrate. In particular disclosed embodiments, the exposure step comprises exposing the substrate and associated mask(s) to oxygen radicals. As the surface of the polymer-coated substrate and the polymer inclusion membrane are hydrophobic, the substrate-polymer surface chemistry can be changed selectively to alter the hydrophobicity by exposing the masked substrate to oxygen radicals (e.g., oxygen radicals generated by an oxygen plasma decontaminator) to facilitate proper interaction with aqueous samples. This exposure step does not alter or damage the chemical assay/polymer inclusion membrane and fixes microfluidic features/patterns on the membranes with high accuracy, even when they have been pre-treated with reagents. In particular disclosed embodiments, oxygen radicals can be generated by an oxygen plasma decontaminator, or other instrument that is capable of generating oxygen radicals. In particular disclosed embodiments, the oxygen plasma decontaminator is used at a power of 13 W Rf (fwd) and at a pressure of 0.6 Torr. These parameters, however, can be modified as needed so as to ensure sufficient exposure/fixation for different fluidic patterns. For example, in embodiments where the device is a flow-through device, the power and exposure time can be increased (e.g., power above 13 W Rf (fwd) and exposure time longer than 5 seconds). The exposure step can be conducted for 2 seconds to 15 seconds, such as 4 seconds to 10 seconds, or 5 seconds or longer. After exposure, the mask (or masks) is removed to reveal the patterned membrane. As the change in chemistry is permanent, the fabricated pattern is also permanent and no significant damage to the assay is observed under the above exposure conditions.

Figure 8:
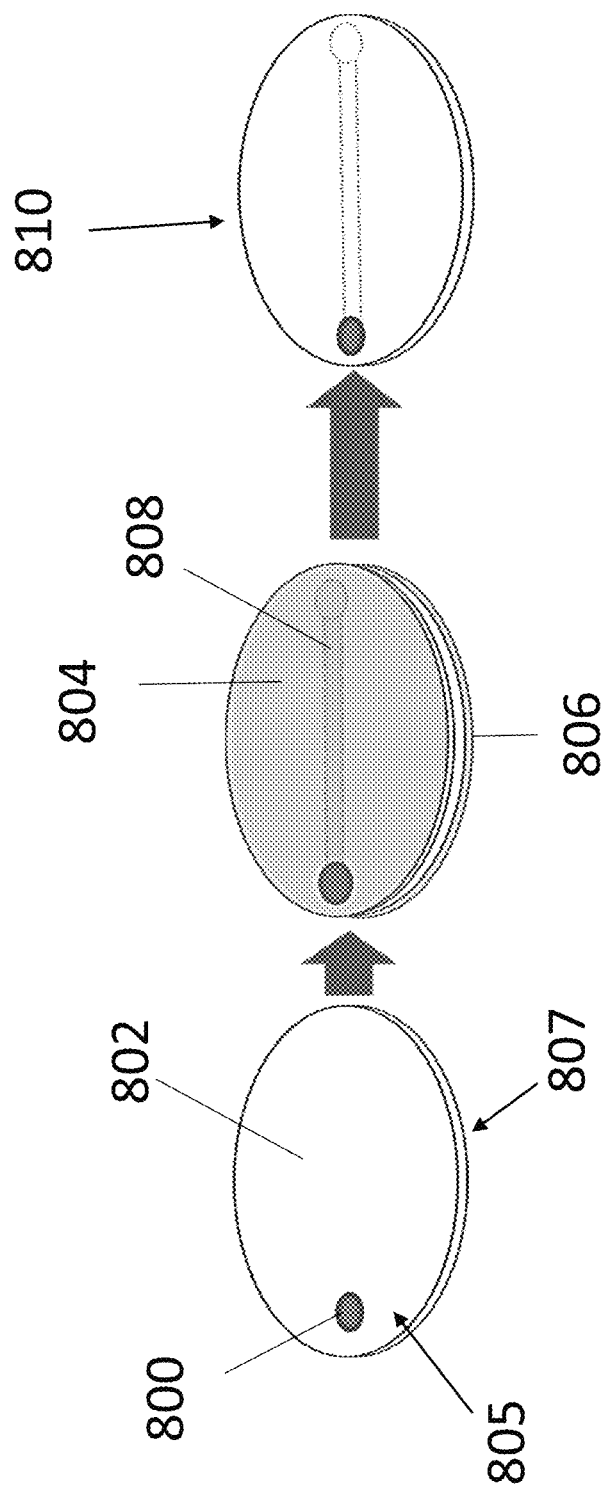
FIG. 8 is a schematic diagram of a method used to make an exemplary flow-through device.
Figure 29:
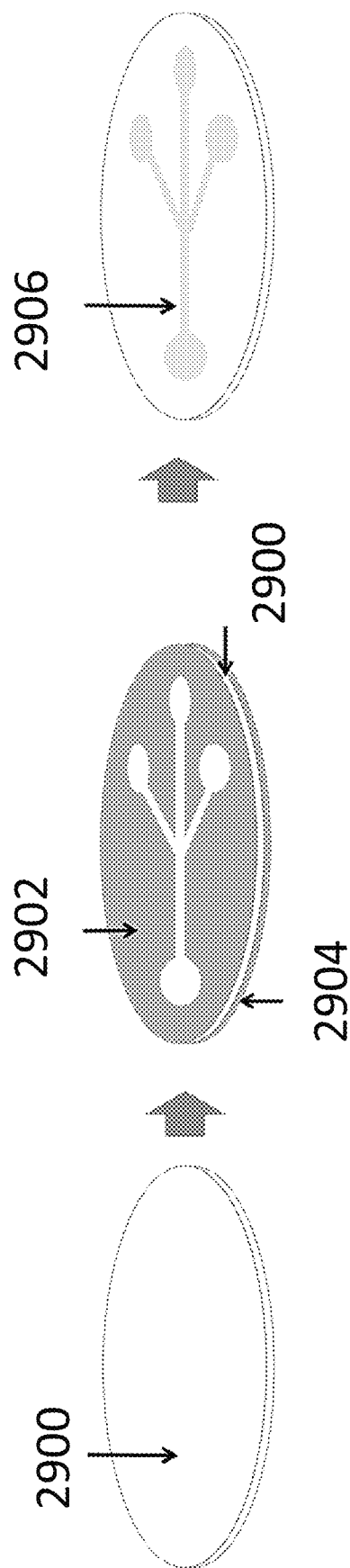
FIG. 29 is a schematic illustration of another exemplary fluidic device embodiment using a substrate (2900) and two masks (2902 and 2904) wherein one mask comprises a branched fluidic channel pattern (2906).

Other method embodiments are contemplated by the present disclosure, such as fabrication methods useful for making fluidic devices that can simultaneously detect the presence (or absence) of multiple different analytes and also simultaneously quantify the amount of each separate analyte that is present. In such embodiments, the methods comprise similar steps as those described above; however, at least one flow-through spot and/or channel is formed in the substrate that allows fluid flow from a top (or first) surface of the substrate to a bottom (or second) surface of the substrate. In some embodiments, only one surface of the substrate comprises a fluidic channel that is fluidly coupled to the flow-through spot/channel. In some embodiments, this configuration can be achieved by using a first mask for a top (or first) surface of the substrate comprising a pattern configured to accept the polymer inclusion membrane spot and a second mask for a bottom (or second surface) of the substrate, which comprises the fluidic channel pattern. As such, any deposited polymer inclusion spot that is added to the substrate where the flow-through spot/channel is located (or that is first deposited followed by generation of the flow-through spot/channel) provides a color development zone where the polymer inclusion membrane can interact with all analytes and produce one or more colors upon interaction with different analytes. Because a flow-through spot/channel is provided, a buffer solution can be added to the devices such that it facilitates flow of the sample through the color development zone to the fluidic channel present on the substrate, which then allows for lateral flow through that fluidic channel. In some embodiments, particular analytes that are soluble in aqueous media will pass through the color development zone and through the fluidic channel, whereas those species that are not soluble will remain at or near the polymer inclusion spot. As such, it is possible to separate the different species and visualize, on one side of the substrate, one analyte species and, on the other side of the substrate, a different analyte species. In exemplary embodiments, heavy metal samples are used and analytical signals from these species are detected. An exemplary flow-through device embodiment is illustrated in FIG. 8. As illustrated in FIG. 8, a polymer inclusion membrane 800 is deposited on a substrate 802. Two masks 804 and 806 are applied to the top surface (805) and bottom (807) surface of the device, respectively. Mask 804 comprises a pattern that accommodates the polymer inclusion membrane and mask 806 comprises the surface lateral flow fluidic channel 808 (mask 804 is illustrated as being transparent so as to show the fluidic channel 808 formed on mask 806). After an exposure step, the masks are removed to provide flow-through device 810. Another exemplary device is illustrated in FIG. 29, which comprises branching lateral flow channels; the process steps for making the device also are illustrated in FIG. 29.

V. Methods of Using Lateral Flow Fluidic Devices

Disclosed herein are methods of using the fluidic devices described herein. The devices disclosed herein can be used for chromatographic separation of analytes in a sample, such as heavy metal analytes, biological analytes, and the like facilitating analyte specific detection. While particular uses are described herein, one unique feature of the disclosed devices is that they can be easily tailored for use in a variety of applications, such as environmental analysis, biological analysis, clinical chemistry, medicinal chemistry, water analysis and quality monitoring, industrial process analysis, food and beverage analysis, and the like. By modifying the polymer inclusion membrane composition, these different types of analyses can be conducted. For example, while some embodiments described herein comprise polymer inclusion membranes comprising a complexation agent suitable for complexing with ionic species, other types of analytical agents can be used depending on the type of analyte to be detected. For example, the polymer inclusion membrane can be modified to include biological probes, such as antibodies, members of specific binding pairs, nucleic acids, and the like. In such embodiments, a suitable detection probe also can be used, such as a dye, a fluorophore, or the like. The disclosed devices comprise polymer inclusion membranes that are deposited as spots and thereby provide the ability to quantitate analytes in the sample by simply visualizing and counting the number of spots that exhibit a color change upon reaction with the analyte. The methods can comprise adding a sample to a substrate, such as to a fluidic channel of the device, a sample pre-treatment section of the device, and/or a flow-through section of the device.

Figure 9:
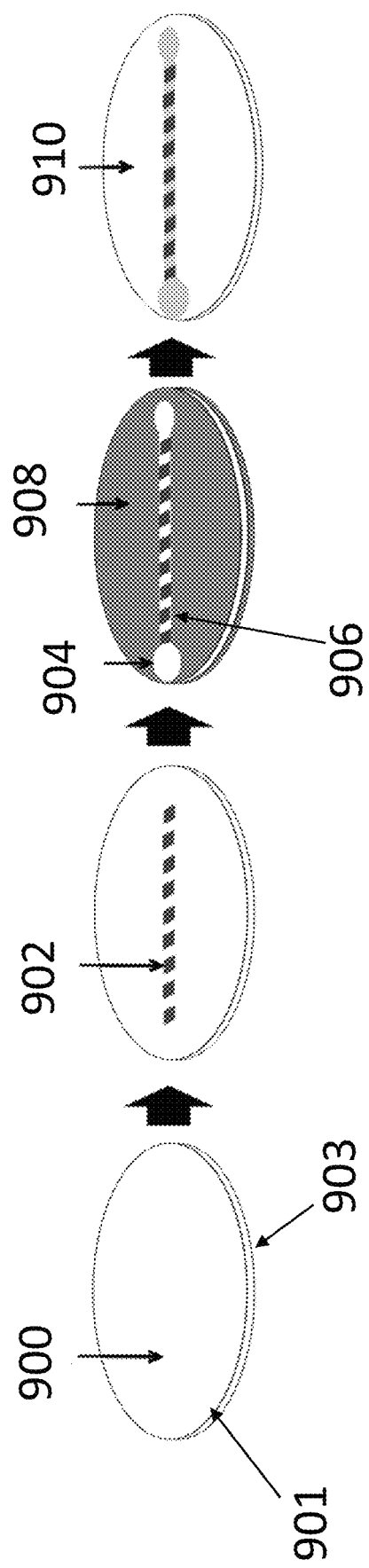
FIG. 9 is a schematic diagram of a method used to make a fluidic device comprising a sample pre-treatment region.

In some embodiments, the fluidic devices can be used for element specific detection of heavy metals. In such embodiments, a pH modification scheme can be used to eliminate interferences that can cause inaccurate detection and quantification of analytes of interest as well as to de-convolute individual analytical signals. In some embodiments, the pH modification schemes can comprise adjusting the pH of the sample being analyzed by including a buffer within the aqueous sample and/or by adding a buffer to the fluidic device, such as in a sample pre-treatment region located adjacent to the fluidic channel of the device. An exemplary device comprising a sample pre-treatment region is illustrated in FIG. 9. According to the method of making device 910, as illustrated in FIG. 9, a substrate 900 having a first surface 901 and a second surface 903 is treated with a polymer inclusion membrane 902, deposited in a desired pattern. A sample pre-treatment section 904 and adjacent fluidic channel 906 are fabricated in the mask 908 that is attached to the substrate. After an exposure step, the mask(s) are removed to provide device 908. The pH modification scheme also can include modifying the pH of the polymer inclusion membrane, such as by immobilizing a buffer on the deposited polymer inclusion membrane; however, the pH should not be modified to be at a pH that deleteriously affects the performance of the polymer inclusion membrane. Modifying the pH can include adjusting the pH to be acidic (e.g., pH 5 or lower, such as pH 4, pH 3, etc.) or adjusting the pH to be basic (e.g., pH above 7, such as pH 8, pH 9, pH 10, etc.). Buffers can be used to maintain the pH above the pH at which the polymer inclusion membrane degrades, such as above pH 3. Buffers typically are selected to be within 1 pH unit of the buffer's respective pKa(s). Examples of suitable buffers include, but are not limited to, phosphate (pKa=2.15, 7.2, 12.33), chloroacetate (pKa=2.88), formate (pKa=3.75), benzoate (pKa=4.2), acetate (pKa=4.76), piperazine (pKa=5.55), MES (pKa=6.21), bis-tris (pKa=6.46) α, PIPES (pKa=7.1), ACES (pKa=6.91), BES (pKa=7.26), MOPS (pKa=7.31), HEPES (pKa=7.66), Tris (pKa=8.06), TAPS (pKa=8.51), ethanolamine (pKa=9.5), CHES (pKa=9.41), CAPS (pKa=10.51), piperidine (pKa=11.12).

In particular disclosed embodiments, such as embodiments where the fluidic devices are used to detect the presence or absence of heavy metals, the pH of the polymer inclusion membrane and/or the aqueous sample being analyzed is adjusted to be acidic, such as pH 5 or lower. In such embodiments, the reactivity between the metal ions present in the sample and the complexation agent can be controlled. For example, at an acidic pH (e.g., pH 5 or lower), only particular metals (e.g., $Cu^{2+}$ and $Co^{2+}$) will complex with the complexation agent so as to provide a chromatographic signal (e.g., color change) that can be visualized with the naked eye. In some embodiments, $Cu^{2+}$ will complex with a complexation agent, such as PAN, to provide a red chromatographic signal and $Co^{2+}$ will complex with a complexation, such as PAN, to provide a green chromatographic signal. Additionally, further differentiation between metal coordination complexes can be obtained as only certain metal coordination complexes are mobile in the aqueous sample, which flows through the fluidic channel. Solely by way of example, a PAN-$Cu^{2+}$ complex is mobile in aqueous flow, whereas PAN-$Co^{2+}$ complexes are not mobile. As such, it is possible to (1) detect the presence (or absence) of cobalt ions in the sample; (2) quantify the amount of cobalt ions in the sample (based on the number of green-colored polymer inclusion membrane spots); (3) detect the presence (or absence) of copper ions in the sample; and (4) quantify the amount of copper ions in the sample. Other metal ions (such as nickel) can likewise form complexes with PAN, though their formation constants and rates of complexation are significantly lower and therefore alternate solution conditions are required for analysis of these targets.

In particular disclosed embodiments, the amount/concentration of copper ions in a sample can be determined by evaluating color changes that occur in the fluidic channel between the different polymer inclusion membrane spots. For example, because PAN-$Cu^{2+}$ complexes are able to move through the fluidic channel because of the complexes' solubility in aqueous solutions, the complexes can be transferred from each polymer inclusion membrane spot to the spaces in between each spot, which results in a color change. In some embodiments, the color change can involve a change from no color, such as when the complexes are not present in the spaces to a colored space (e.g., red or pink) when the complexes are present. Using the number of color change regions present between spots of the polymer inclusion membrane, the concentration of the copper ions can be determined. In some embodiments, the concentration can be proportional to the observed color intensity.

Figure 10:
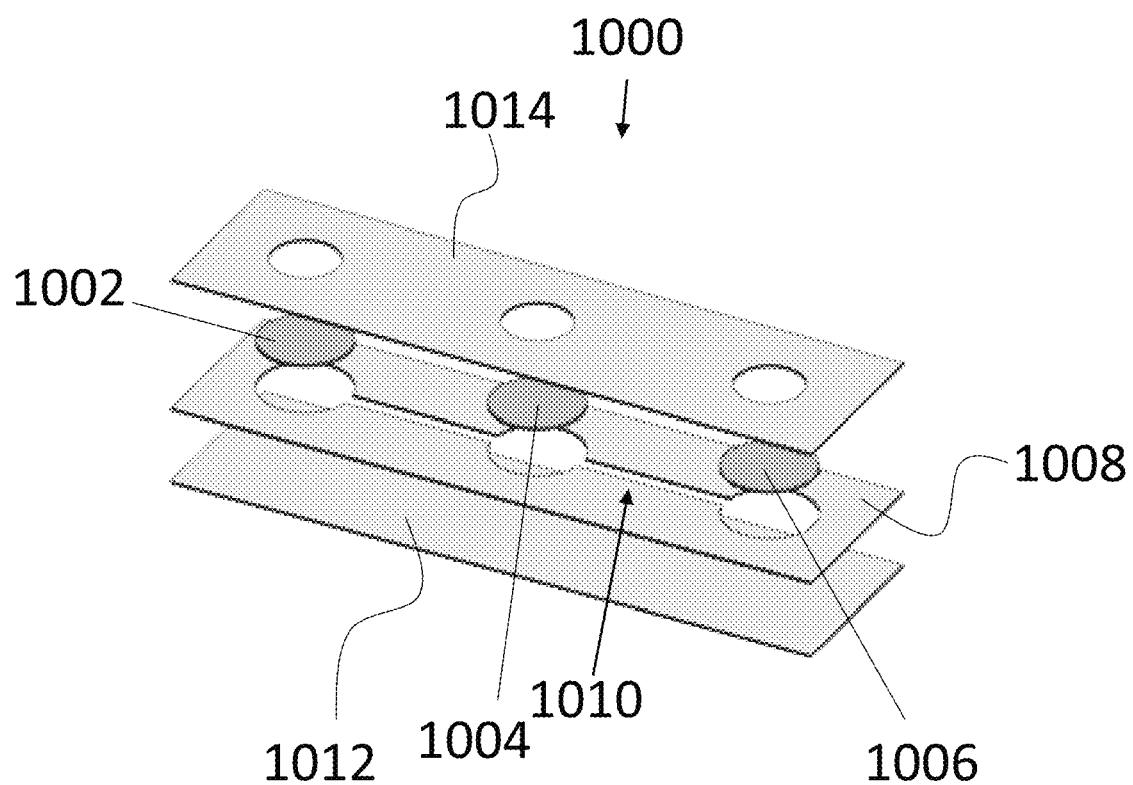
FIG. 10 is an exploded perspective view of an exemplary device that can comprise a plurality of substrates treated with polymer inclusion membranes and varying pH values.
Figure 11:
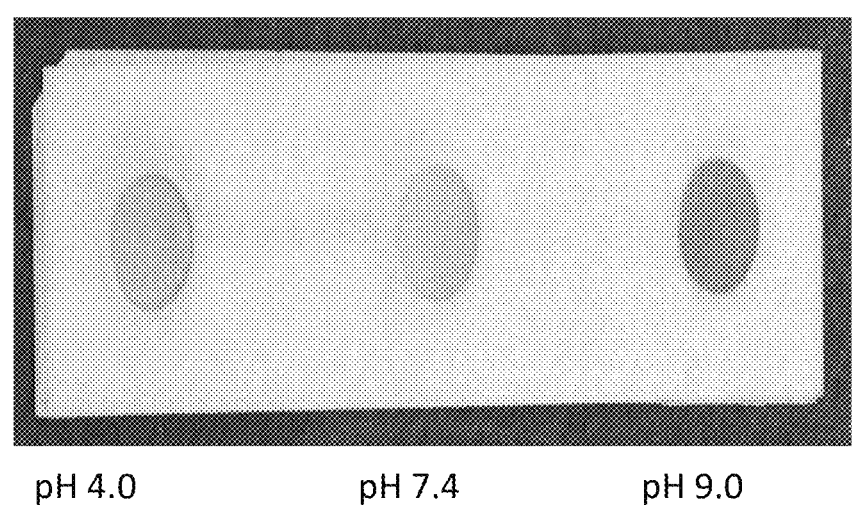
FIG. 11 is a photographic image of results obtained from analyzing a sample using a device similar to the device of FIG. 10.

In some embodiments, a pH gradient can be used to provide multiple metal ion detection. In embodiments utilizing a pH gradient, a plurality of polymer inclusion membrane-treated substrates that have been treated under different buffer conditions to provide substrates with different pH values can be used. The plurality of substrates can be fluidly connected through a fluidic channel formed in a fluidic platform configured to house the plurality of substrates. For example, the fluidic device can comprise one or more layers of a polymer-coated substrate (e.g., PCL coated paper), wherein at least one of the layers comprises a fluidic channel that is fluidly coupled to spaces configured to house the plurality of polymer inclusion membrane-treated substrates. In some embodiments, a top and bottom layer is used and the fluidic channel-containing substrate is placed between these two layers. The polymer inclusion membrane-treated substrates are then placed in the spaces of the device. The plurality of polymer inclusion membrane-treated substrates can be positioned in any desired geometry, such as linearly, branched, circularly, or the like. The pH sensitive polymer inclusion membranes will react with different metal ions at different pH values. In some embodiments, the sample being analyzed can be added to the polymer inclusion membrane-treated substrate that has been treated to have the lowest pH. The sample will laterally flow to the next adjacent pH sensitive polymer inclusion membrane spot, which has a higher pH. This type of flow continues until all ions have been consumed at the particular pH at which they react with the complexation agent of the polymer inclusion membrane. This method allows the analyte to interact with the polymer inclusion membrane spot for an adequate time so that all the metal ions are consumed at their preferred pH. As the colored complexes formed are solids, they are trapped in the substrate, limiting interferences at higher pH. An exemplary embodiment of this fabrication method is illustrated in FIG. 10. With reference to FIG. 10, device 1000 is constructed to comprise a plurality of polymer inclusion membrane-treated substrates 1002, 1004, and 1006, wherein each has a different pH. A fluidic channel-containing substrate 1008 is configured to house polymer inclusion membrane-treated substrates 1002, 1004, and 1006 and also to comprise a fluidic channel 1010 that fluidly couples the polymer inclusion membrane-treated substrates. The fluidic channel-containing substrate 1008 is positioned between a bottom layer 1012 and a top layer 1014. The assembly may be thermally laminated, although other means of assembly such as solvent welding, ultrasonic welding, and laser welding are likewise possible and have been demonstrated. This general approach to fabrication is extensible to other polymers, which provides further flexibility with regard to solvent selection for solvent welding, temperature for thermal lamination, and lasing parameters for laser welding. FIG. 11 provides a photographic images of results obtained from analysis using a representative device.

Figure 12A:
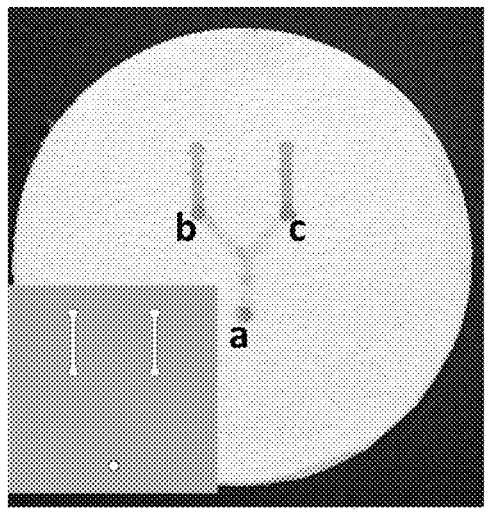
FIGS. 12A and 12B are photographic images of an exemplary multidimensional flow-through/lateral surface flow device, with FIG. 12A showing the top surface of the device and FIG. 12B showing the bottom surface of the device.
Figure 12B:
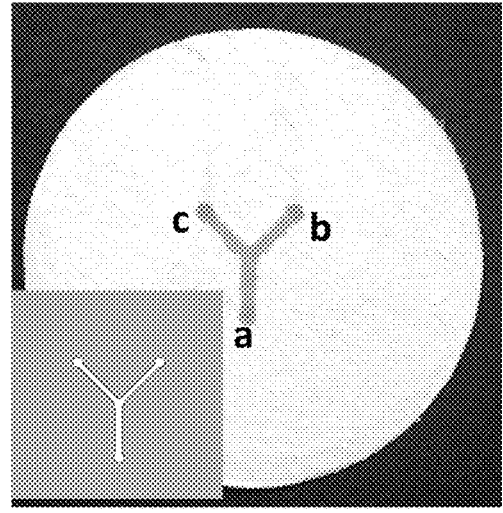
Figure 13A:
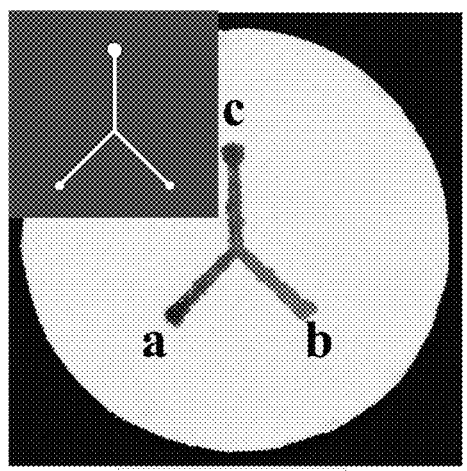
FIGS. 13A and 13B are photographic images of an exemplary mixing device, with FIG. 13A showing the top surface of the device and FIG. 13B showing the bottom surface of the device.
Figure 13B:
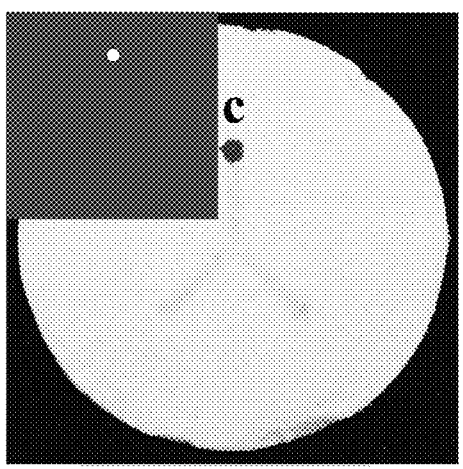
Figure 16:
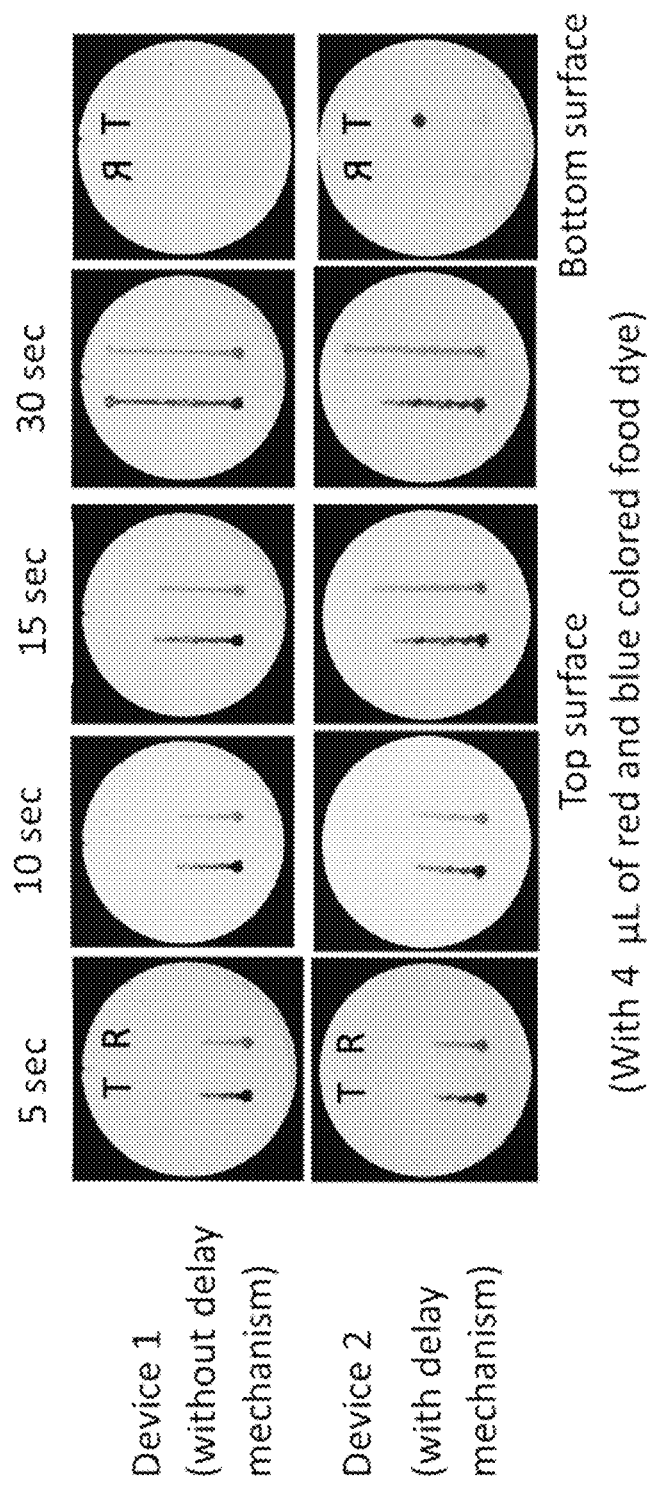
FIG. 16 includes photographic images of an exemplary device having a delay mechanism to provide a microfluidic delay circuit.

In yet additional embodiments, the fluidic devices described herein can be used as filtration and separation platforms for samples and/or reagents. In such embodiments, the device can be configured to comprise at least one flow-through spot and one or more fluidly coupled surface-lateral flow channels. An exemplary embodiment of such a device is illustrated in FIGS. 12A and 12B. This device demonstrates the capability of the disclosed fabrication methods to generate 3-dimensional fluid flow patterns on/in a single substrate, such as flow-through fluid flow patterns (e.g., from the top of the substrate through to the bottom of the substrate) in combination with lateral surface flow on the bottom of the substrate; or flow-through fluid flow patterns (e.g., from the bottom of the substrate through to the top of the substrate) in combination with lateral surface flow on the top of the substrate. As can be seen by FIG. 12A, two flow-through spots are fabricated into the top surface of the substrate, which are fluidly coupled to surface-lateral flow channels that have been made in the bottom surface of the substrate (FIG. 12B). Additional embodiments of multidimensional fluidic devices are illustrated in FIGS. 13A/13B, 14, 15A/15B, 16, and 17, with some embodiments allowing for microfluidic mixing (FIGS. 13A and 13B) and/or separation (FIGS. 14 and 15A and 15B), as well as some embodiments acting as microfluidic delay circuits (FIG. 16), microfluidic timer circuits, and volume controlling gates. In examples where the device is used for filtration/separation, the device can be used to separate fluids having mixed hydrophilic and hydrophobic properties (FIGS. 17A and 17B). The superhydrophilic fluidic channels of the device will attract the aqueous layer and transfer it rapidly through the fluidic channel while the hydrophobic fluid remains behind. Additional examples of devices contemplated by the present disclosure are shown in FIGS. 18A and 18B, which shows a flow-through device having a fluidic channel on a top surface (FIG. 18A) and spot developed through the membrane so as to deliver sample to a bottom surface (FIG. 18B) comprising a channel) and FIGS. 19A and 19B, which shows a surface-lateral flow device having different fluidic channel patterns on the top surface (FIG. 19A) and the bottom surface (FIG. 19B).

Samples that can be used and evaluated with the disclosed devices include aqueous samples comprising ionic species, such as heavy metal; biological samples comprising ionic species; and organic samples. Any amount of sample can be used with the disclosed devices, as long as the channel dimensions and geometry can accommodate the sample. Solely by way of example, if lateral surface flow channels are included on the device and have dimensions of 0.75 mm×25 mm, then about 5 µL to 10 µL of sample can be used. Device embodiments comprising such lateral surface flow channels in combination with a flow-through channel can tolerate more sample, such as 25 µL to 50 µL.

In some embodiments, optical filter masks can be used in combination with the devices for deconvolution of multiple signals in a single channel, thus allowing for non-specific complexing agents to be used in a way not contemplated by conventional devices. Examples of using an optical filter are described below. The absorption range of the optical filter can be selected to provide visualization of a particular color of interest.

VI. Examples

PCL-Filled GMF Membranes

PCL solutions (w/v) were prepared by dissolving appropriate weights of PCL (Perstorp, Warrington, UK) in appropriate volumes of analytical grade toluene (Macron Fine Chemicals, Center Valley, Pa., USA). Solutions were spin-coated (Laurell WS-400, North Wales, Pa., USA) at 2500 rpm for 30 seconds on Whatman (GE Healthcare Bio-Sciences, Pittsburgh, Pa., USA) glass microfiber (GF/A) membranes followed by drying at 50° C. for 15 min. The initial weight percentage of PCL: GMF was approximately 50:50 under the above conditions.

Surface Modification of PCL-Filled GMF

PCL-filed GMF was treated with 25% (v/v) trimethylchlorosilane (TMCS) (Alfa Aesar, Ward Hill, Mass., USA) and acetone (technical grade) under room temperature for 4 hrs. Then treated membranes were soaked in 100% acetone to remove excess TMCS (1 hr) followed by washing with excess acetone. Then the membranes were let dry at room temperature (>24 hrs).

Preparation of Masks

The desired mask for each surface (top and bottom) was designed using drafting software (SolidWorks 2013-2014 Education edition, Waltham, Mass., USA) and cut on tape (i tape, Intertape Polymer Group, Marysville, Mich., USA) using a laser cutter (VLS 3.50, Universal Laser Systems, Scottsdale, Ariz., USA).

Preparation of Polymer Inclusion Membrane and Dispensing

Polymer inclusion membrane is prepared by dissolving 0.005 g of 1-(2-pyridylazo)-2-naphthol (PAN) (Alfa Aesar, Mass., USA), 0.040 g N,N'-bis(3,5-di-tert-butylsalicylidene)-1,2-cyclohexanediaminomanganese(III) chloride (Jacobsen's catalyst) (Strem Chemicals, MA, USA), 0.100 g PCL (Perstorp, Warrington, UK) and Bis-2-ethyl sebacate (TCI America, Portland, Oreg., USA) in 10 mL of Toluene (Avantor, Pa., USA). The dispensing of the assay was done using a digital solution dispenser (HP D300 Digital Dispenser, Hewlett Packard, Palo Alto, Calif., USA). The volume of dispensing was determined by the required conditions.

Oxygen Radical Exposure Embodiments

Figure 28:
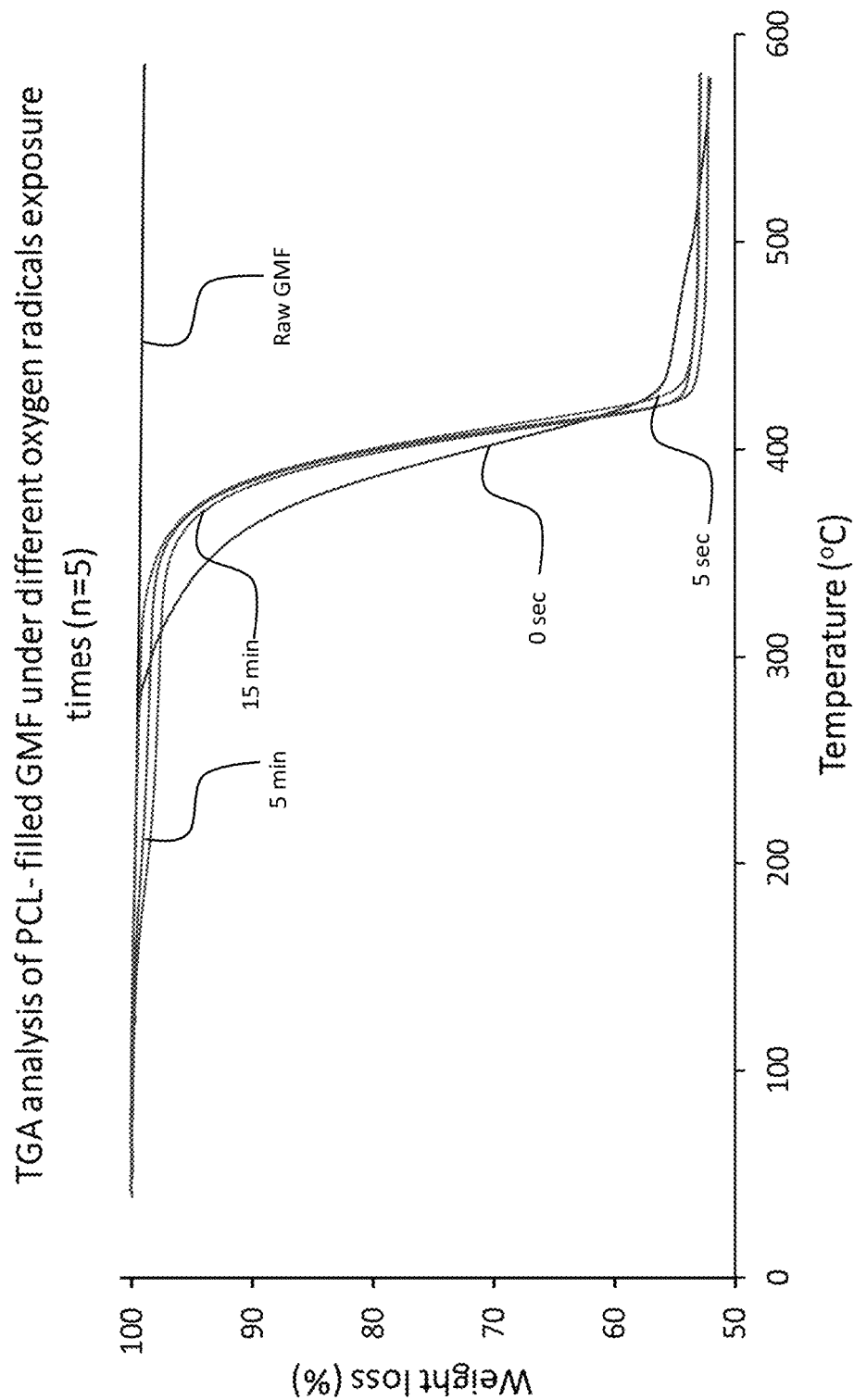
FIG. 28 is a graph of mass loss as a function of temperature, which shows results obtained from thermogravimetric analysis of a polymer-coated substrate at different radical exposure times.

Oxygen radical exposure examples were conducted using an Evactron (Redwood City, Calif., USA) decontaminator/RF plasma cleaner under conditions determined separately for each experiment. The pressure and forward RF power were maintained at constant values of 0.6 Torr and 13 W, respectively. Selective exposure to radicals was accomplished by covering the area of the membrane intended to remain unexposed with a patterned mask, prepared as described above. Exemplary results obtained from such embodiments are shown in FIG. 28. FIG. 28 shows results from TGA analysis, which was used to evaluate whether or not etching of the PCL/PIM occurs under the exposure conditions. As can be seen by FIG. 28, no etching occurred during the exposure time used during fabrication.

Preparation of Buffers and Other Solutions

All solutions were prepared using distilled deionized water (Milli-Q Advantage A10).

pH 3: Dissolved 0.0637 g of formic acid ammonium salt (Alfa Aesar, Ward Hill, Mass., USA) in 100 mL of distilled DI water, the pH was adjusted to 3.0 with 1 M HCl (Macron Fine Chemicals, Center Valley, Pa., USA).

pH 4 and pH 5: Dissolved 0.06 g of glacial acetic acid (Fisher chemicals, Fair Lawn, N.J., USA) in 100 mL of distilled DI water, the pH was adjusted to relevant pH with 1 M NaOH (Mallinckrodt, Paris, Ky., USA).

pH 8: Dissolved 0.0121 g of Tris base (VWR international, West Chester, Pa., USA) in 100 mL of distilled DI water, the pH was adjusted to 8.0 with 1 M HCl (Macron Fine Chemicals, Center Valley, Pa., USA).

pH 9: Dissolved 0.061 g of Ethanolamine (Alfa Aesar, Ward Hill, Mass., USA) in 100 mL of distilled DI water, the pH was adjusted to 9.0 with 1 M HCl (Macron Fine Chemicals, Center Valley, Pa., USA).

The following chemicals were also used in this study: ACS grade $CuCl_2 \cdot 2H_2O$, $MnSO_4 \cdot H_2O$, $ZnCl_2$ (Mallinckrodt, Paris, Ky., USA), $Pb(NO_3)_2$ (Sigma-Aldrich, St. Louis, Mo., USA), Analytical grade NaCl, $CoCl_2 \cdot 6H_2O$, $CdCl_2$ (Fluka Chemical Corporation, Ronkonkoma, N.Y., USA), $FeCl_3$ (98%) (EMD Chemicals, Gibbstown, N.J., USA), $NiCl_2$ (99.99%), Formic acid (99%) (Alfa Aesar, Ward Hill, Mass., USA)

Example 1

As disclosed herein, PAN-$Cu^{2+}$ complexes are soluble in water at low pH, below pH 7, yet the polymer inclusion membrane itself is not specific for the $Cu^{2+}$; therefore, to evaluate the specificity of $Cu^{2+}$ detection, a fluidic device and pH modification scheme was conducted with common heavy metal ions in environmental/drinking water. The test was conducted under different pH to investigate the pH dependence solubility of PAN-$M^{n+}$. As shown in FIGS. 20A and 20B, the assay itself is not specific for $Cu^{2+}$ at higher pH (FIGS. 20A and 20B) as $Co^{2+}$, $Cu^{2+}$, $Zn^{2+}$, $Cd^{2+}$, $Mn^{2+}$ also exhibit color changes on the polymer inclusion membrane assay. Interestingly, at lower pH (below 5.0), only $Cu^{2+}$ and $Co^{2+}$ cause the color change; however, only the PAN-$Cu^{2+}$ complex moved with the aqueous sample flow. An additional embodiment is illustrated in FIGS. 20C and 20D, which show the effect of the pH on the interaction of $M^{n+}$ with the PAN-containing polymer inclusion membrane. As can be seen by FIGS. 20C and 20D, at lower pH only $Cu^{2+}$ and $Co^{2+}$ form complexes with PIM (FIG. 20C) but at higher pH (pH 8), $Cu^{2+}$, $Co^{2+}$, $Ni^{2+}$, $Zn^{2+}$, $Cd^{2+}$, $Mn^{2+}$ form colored complexes (FIG. 20D). Therefore, this example establishes that it is possible to use pH adjustment to reduce any particular competition over $Cu^{2+}$ that may be caused by the presence of other metal ions in the sample. The fluidic devices are thus able to use color migration to specifically detect $Cu^{2+}$ despite of the presence of other metal ions.

Example 2

Figure 21:
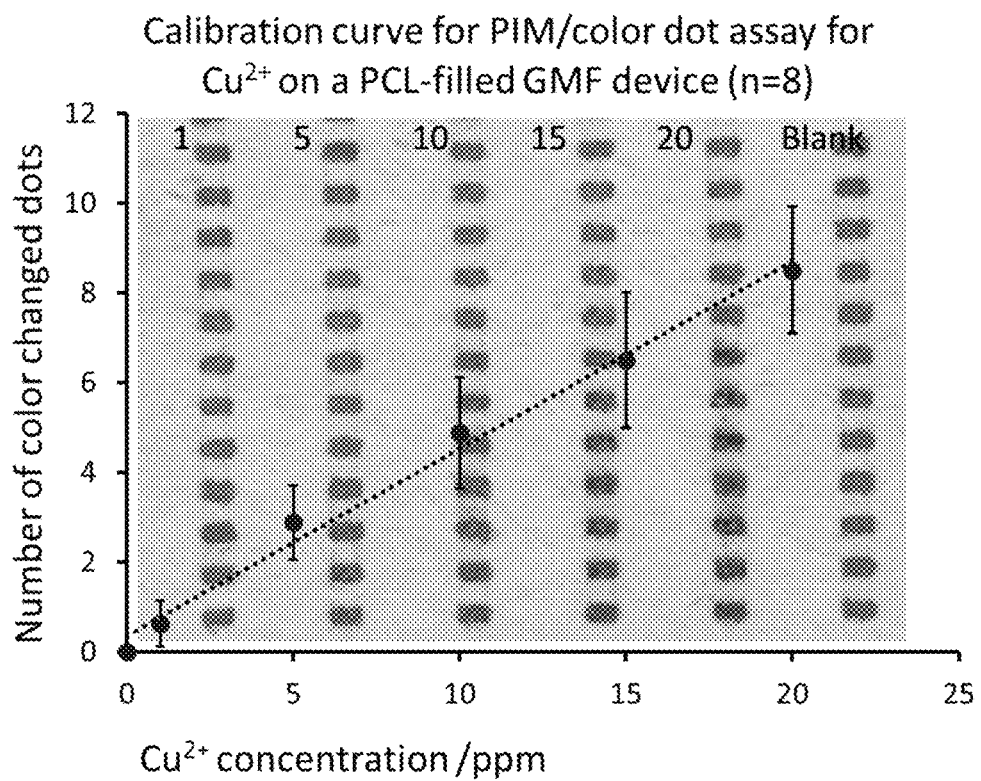
FIG. 21 is a calibration curve obtained from analysis of a polymer-coated device embodiment treated with a sample comprising copper ions.
Figure 22:
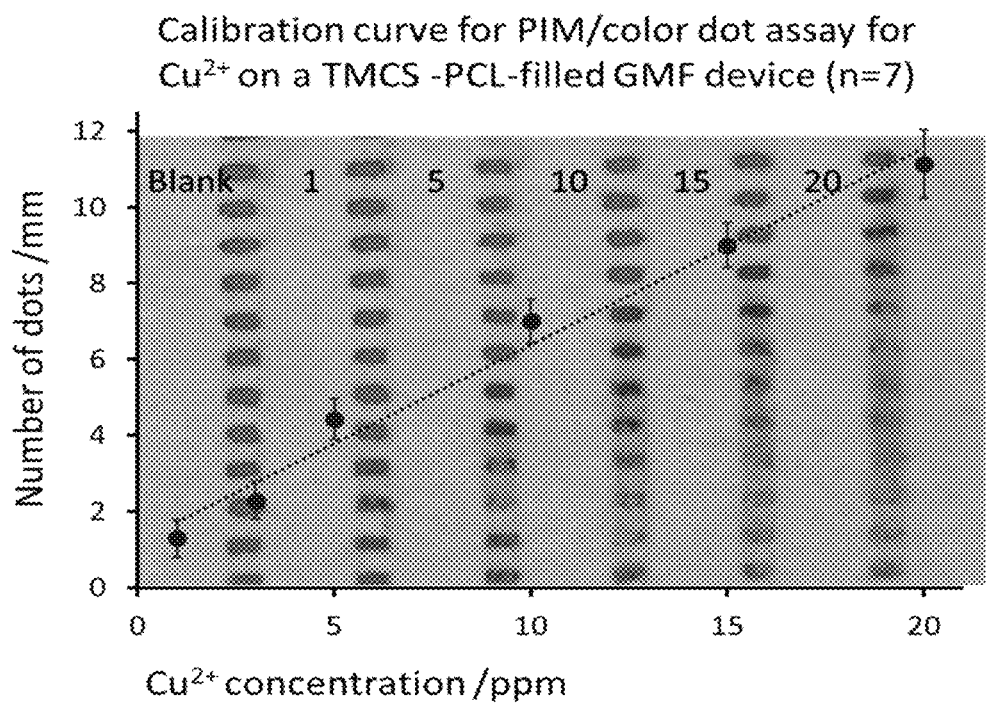
FIG. 22 is a calibration curve obtained from analysis of a polymer-coated device embodiment that is surface-modified with a TMSCl reagent and then treated with a sample comprising copper ions.

In this example, the concentration dependence of color changed areas (areas located between the dispensed polymer inclusion membrane spots) were studied. The pH of the test solutions was kept acidic (pH 4.5) to eliminate unfavorable interferences. As shown in FIG. 21, a good linear relationship was observed within the $Cu^{2+}$ concentrations of 1 ppm (15.7 µM) to 20 ppm with the $R^2$>0.99 using very low sample volumes (5 µL). This is within the maximum allowable concentration of $Cu^{2+}$ in drinking water; therefore, this approach is highly suitable for detection of $Cu^{2+}$ in drinking as well as environmental waters. It was also observed that the resolution and the detection limits of this can be tuned by adjusting the dispensation of spots of the polymer inclusion membrane on the substrate, as well as by adjusting the flow channel dimensions. Another calibration curve from an exemplary embodiment utilizing a TMS-functionalized substrate is shown in FIG. 22.

Example 3

In this example, surface modification was used to reduce the effects of exposed silanol groups. TMSCl was used to modify a PCL-filled GMF substrate, using a surface modification procedure as outlined above. As shown in FIG. 23B, the TMS modified membrane showed higher efficiency, as observed by the migrating PAN-$Cu^{2+}$ complex. In another example, a pH modification scheme was used to achieve high efficiency with an unmodified substrate (FIG. 23A). FIG. 24A provides a photographic image of a substrate (GMF) that was not modified with TMSCl and FIG. 24B provides a photographic image of a substrate (GMF) treated with TMS.

Example 4

Figure 25:
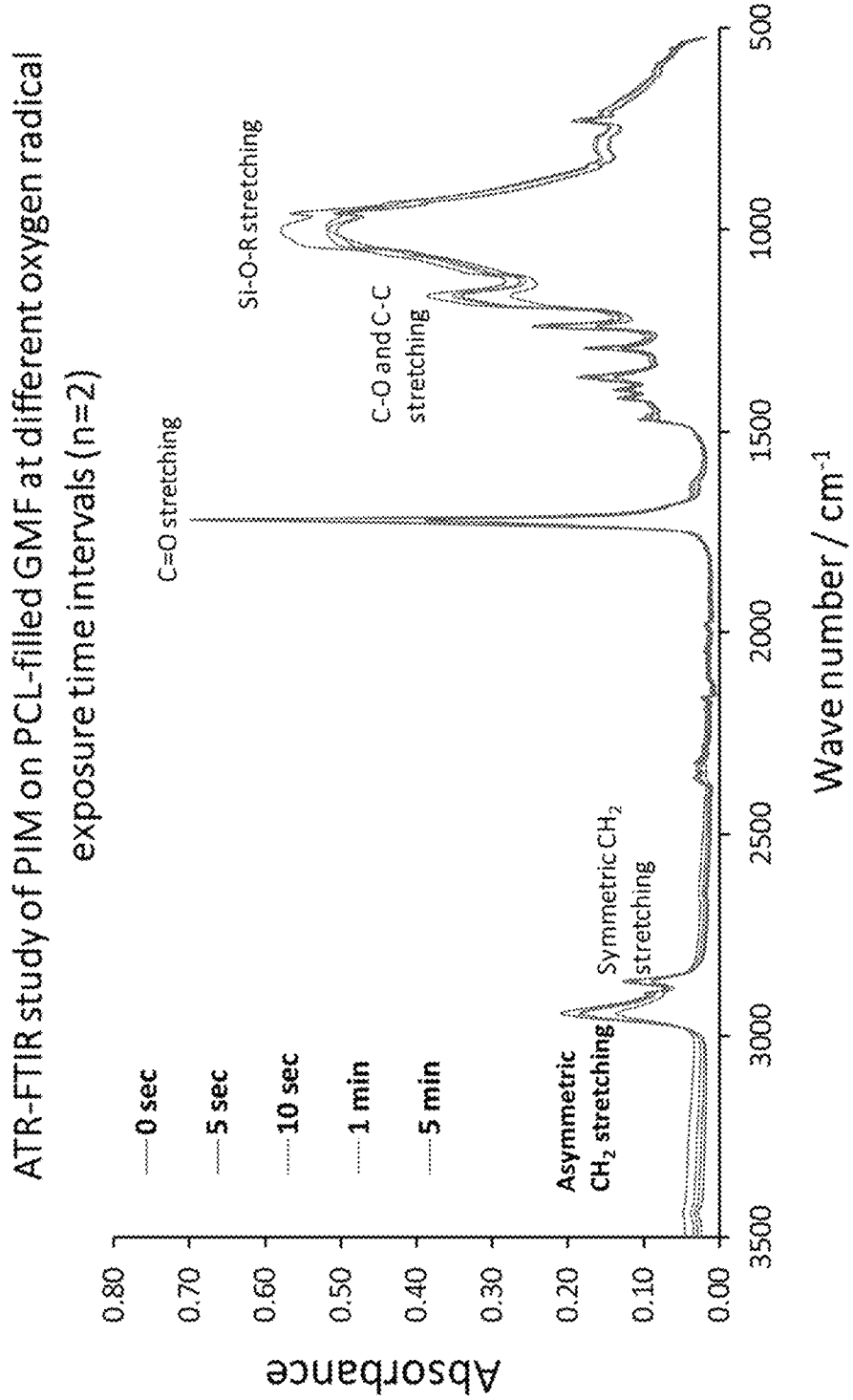
FIG. 25 is a graph of absorbance as a function of wavenumber illustrating structural features of a polymer-coated substrate at different oxygen radical exposure time intervals.

In this example, the effect of an oxygen radical exposure step on the molecular chemistry of bulk polymer inclusion membrane was evaluated. ATR-FTIR spectra were taken and analyzed for any significant chemistry differences. Interestingly, nearly identical spectra were observed from 0 seconds (not exposed) to 5 minutes for exposed PIM dispensed PCL-filled GMF membranes, confirming that the exposure to oxygen radicals does not change the chemistry (FIG. 25). The Si—O stretching signal was observed at the finger print region of every spectra due to overlap of background signal produced by the GMF substrate.

Example 5

Figure 26A:
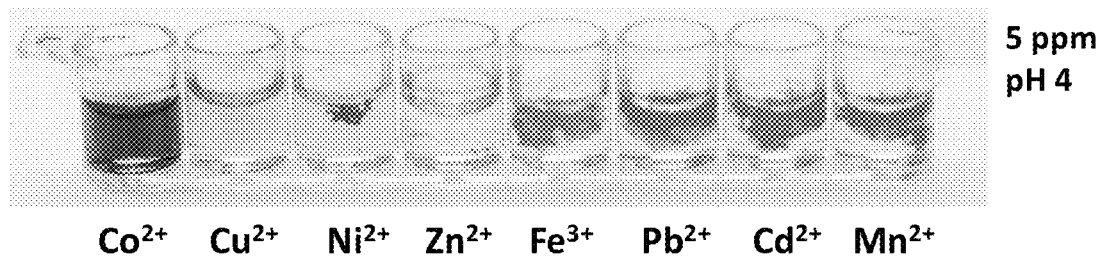
FIGS. 26A-26C are photographic images of results obtained from a pH gradient scheme.
Figure 26B:
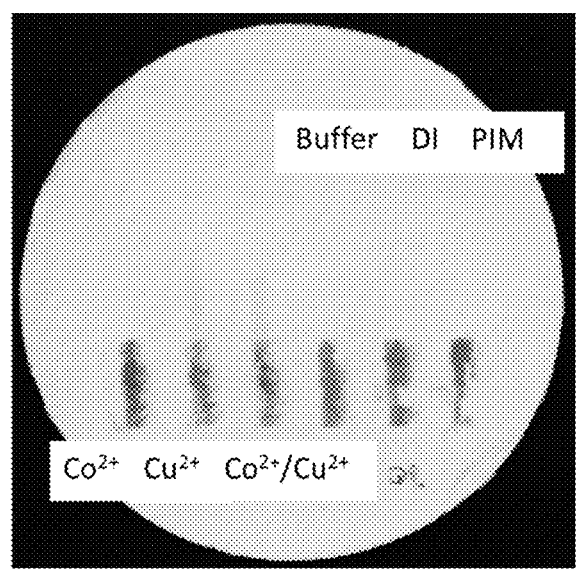
Figure 26C:
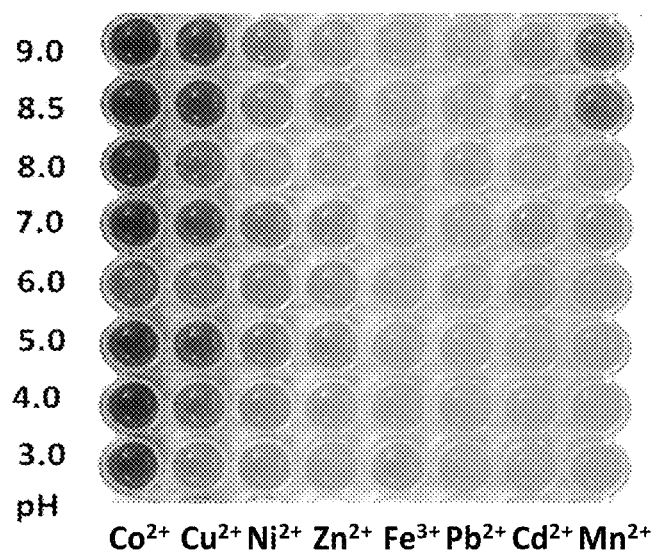
Figure 27A:
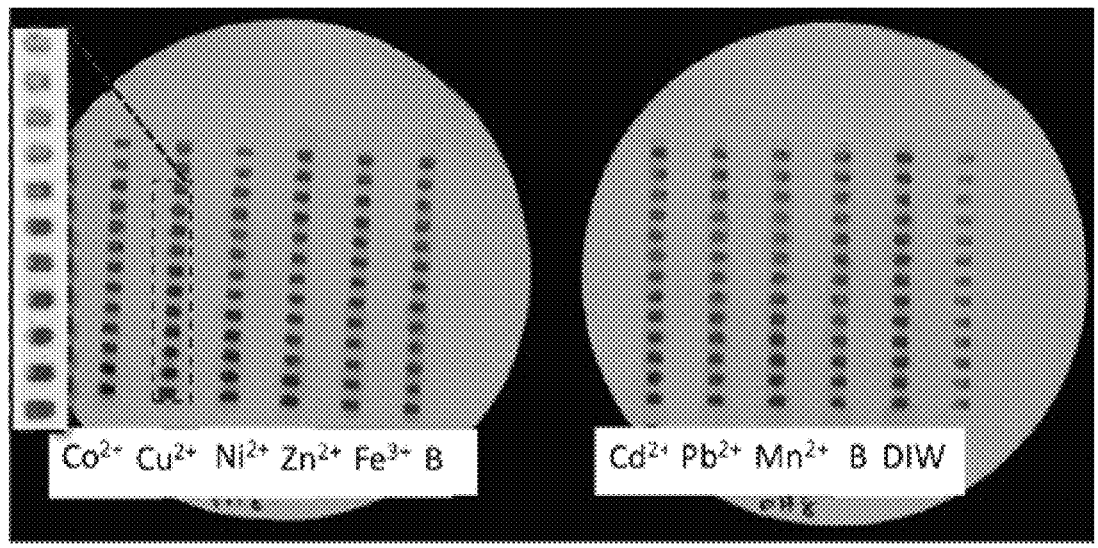
FIGS. 27A-27G are photographic images of exemplary device embodiments showing how chromatographic signals can be selectively detected on a device using visual detection (FIGS. 27A and 27E), a device using a color mask (FIGS. 27B and 27F), a device using greyscale visualization (FIG. 27C), and surface lateral flow (FIG. 27D)
Figure 27B:
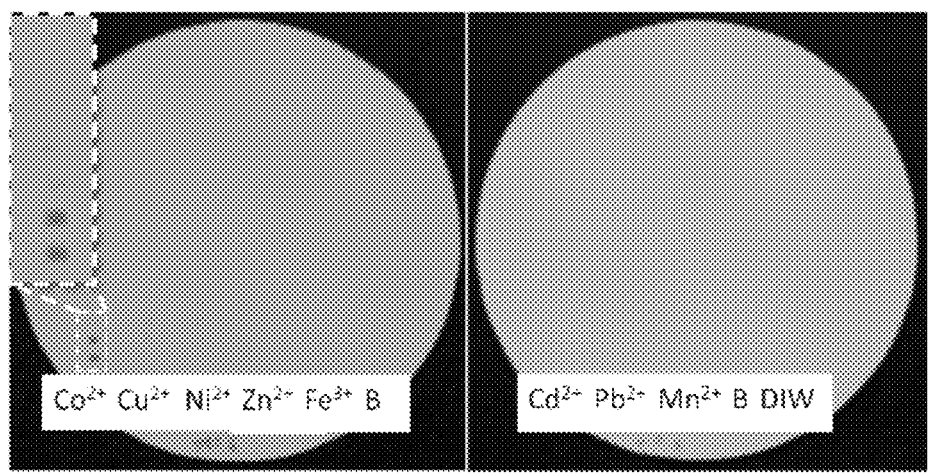
Figure 27C:
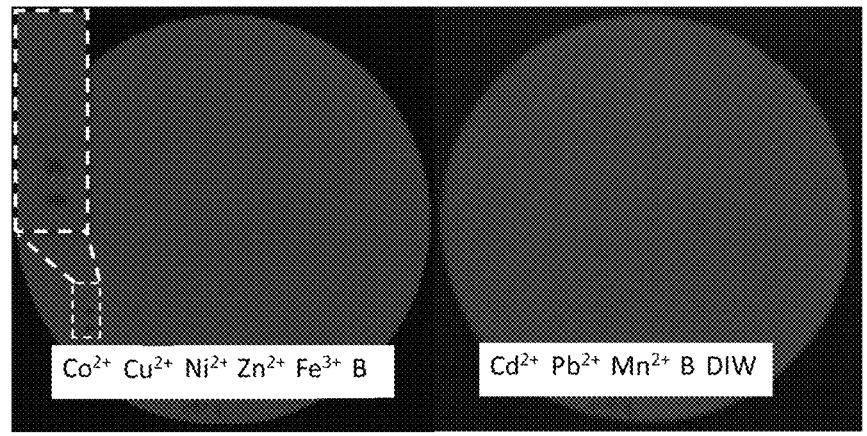
Figure 27D:
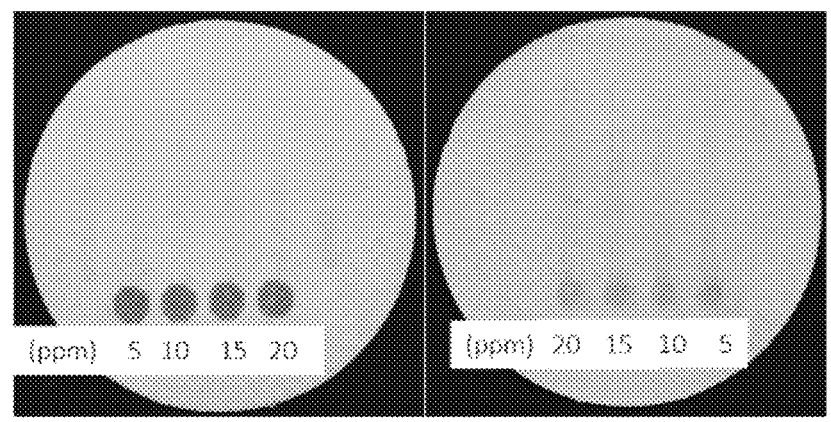
Figure 27E:
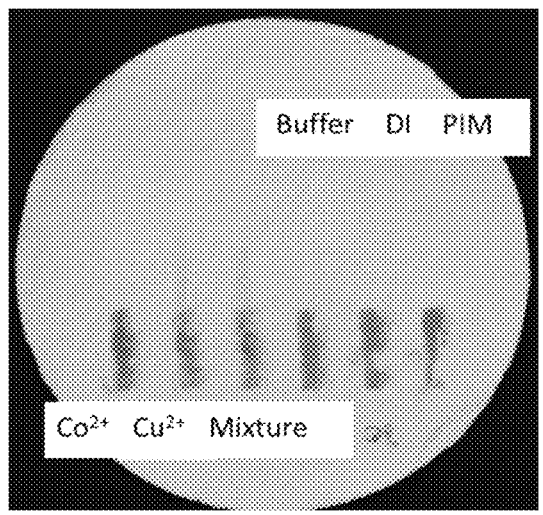
Figure 27F:
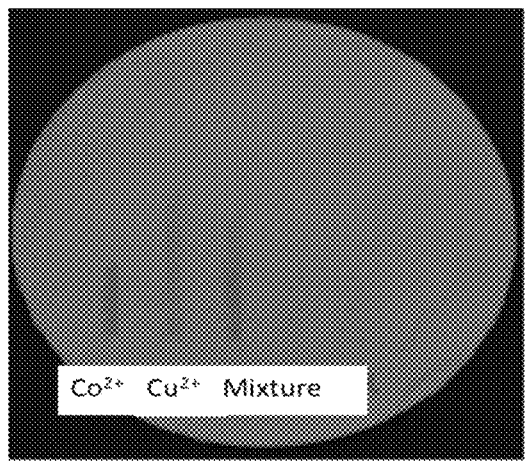
Figure 27G:
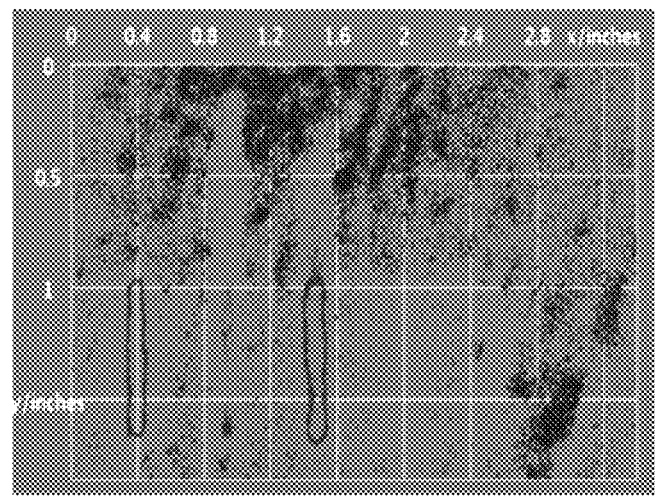

In this example, a pH gradient scheme is assessed to evaluate the ability to eliminate interferences using the pH gradient. A well plate is treated with solutions of different metal ions at a range of pH values and also includes PAN. As illustrated in FIGS. 26A and 26B, PAN reacts with certain species (e.g., $Co^{2+}$ and $Cu^{2+}$) readily at pH 4.0, while other metals do not react at all or are slow (e.g., $Ni^{2+}$). Additionally, FIG. 26B shows that $Cu^{2+}$ is able to flow with the sample, while $Co^{2+}$ is retained on the polymer inclusion membrane. This type of detection also can be used to separate the two ions using a flow-through device embodiment as described herein, which can separate the $Cu^{2+}$ ions on one surface of the substrate with the $Co^{2+}$ ions located on the other surface of the substrate (FIG. 27D). Optical separation also is feasible using color filters (e.g., as can be seen in FIG. 27B). Also as illustrated in FIG. 26C, different colors are produced at different pH values and the amount of the formed PAN-$M^{n+}$ can be controlled by varying the pH.

Example 6

In this example, the use of an optical color filter to mask out unwanted colors was explored. FIGS. 27A-27C illustrate results obtained from this example. FIG. 27A shows a raw image of an exemplary device after sample deposition. FIG. 27B shows that only the PAN-$Co^{2+}$ color is visible through a ~580 nm absorption filter which can be enhanced by converting that image into gray scale (FIG. 27C). FIG. 27D shows color separation on a PCL-filled GMF platform tested with $Co^{2+}$ and $Cu^{2+}$ at pH 4.5 (5 µL of $Co^{2+}$ and $Cu^{2+}$ followed by 5 µL of buffer).

VII. Overview of Several Embodiments

Disclosed herein are embodiments of fluidic devices, comprising a substrate having a first surface and a second surface; an optional polymeric coating that coats or substantially coats the substrate; one or more fluidic channels defined on the first surface of the substrate, the second surface of the substrate, or both; and one or more polymer inclusion membrane spots positioned within the one or more fluidic channels.

In any or all embodiments, the substrate is a hydrophilic, porous substrate.

In any or all of the above embodiments, the substrate is a hydrophobic substrate and the optional polymeric coating is not present.

In any or all of the above embodiments, the substrate is a paper substrate, a glass microfiber substrate, or a combination thereof.

In any or all of the above embodiments, the substrate has a thickness ranging from 115 µm to 675 µm.

In any or all of the above embodiments, the polymeric coating comprises a polymer having a formula

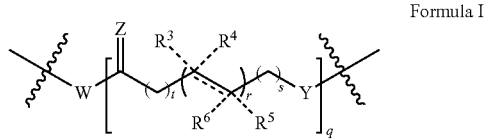

Formula I wherein Z, Y, and W independently are selected from O, S, NH, and NR², where R² is selected from hydrogen, aliphatic, aryl, and heteroaryl; $R^3$, $R^4$, $R^5$, and $R^6$ (if present) independently are selected from hydrogen, aliphatic, aryl, heteroaryl, and a heteroatom-containing moiety selected from halogen, aldehyde (—$R^a$CHO), acyl halide (—$R^a$C(O)X) (where X is selected from fluorine, chlorine, bromine, and iodine), carbonate (—$R^a$OC(O)O$R^b$), carboxyl (—$R^a$C(O)OH), carboxylate (—$R^a$COO⁻), ether (—$R^a$O$R^b$), ester (—$R^a$C(O)O$R^b$, or —$R^a$OC(O)$R^b$), hydroxyl (—$R^a$OH), ketone (—$R^a$C(O)$R^b$), silyl ether ($R^b R^c R^d$SiO$R^a$—), peroxy (—$R^a$OO$R^b$), hydroperoxy (—$R^a$OOH), phosphate (—$R^a$OP(O)(OH)$_2$), phosphoryl (—$R^a$P(O)(OH)$_2$), phosphine (—P$R^a R^b R^c$), thiol (—$R^a$SH), thioether/sulfide (—$R^a$SR), disulfide (—$R^a$SS$R^b$), sulfinyl (—$R^a$S(O)$R^b$), sulfonyl (—$R^a$SO$_2 R^b$), carbonothioyl (—$R^a$C(S)$R^b$ or —$R^a$C(S)H), sulfino (—$R^a$S(O)OH), sulfo (—$R^a$SO$_3$H), thiocyanate (—$R^a$SCN), isothiocyanate (—$R^a$NCS), oxazole, oxadiazole, imidazole, triazole, tetrazole, amide (—$R^a$C(O)N$R^b R^c$, or —$R^a$N$R^b$C(O)$R^c$), azide (N$_3$), azo (—$R^a$NN$R^b$), cyano (—$R^a$OCN), isocyanate (—$R^a$NCO), imide (—$R^a$C(O)N$R^b$C(O)$R^c$), nitrile (—$R^a$CN), isonitrile (—$R^a$N⁺C⁻), nitro (—$R^a$NO$_2$), nitroso (—$R^a$NO), nitromethyl (—$R^a$CH$_2$NO$_2$), and amine (—$R^a$NH$_2$, —$R^a$NH$R^b$, —$R^a$N$R^b R^c$), wherein $R^a$ is absent, aliphatic, aryl, heteroaliphatic, or heteroaryl; $R^b$, $R^c$, and $R^d$ independently are hydrogen, aliphatic, aryl, heteroaliphatic, heteroaryl, and any combination thereof; r is from 1 to 4; s and t independently range from 0 to about 4; and q ranges from at least 1 to about 1000.

In any or all of the above embodiments, the polymeric material has a formula

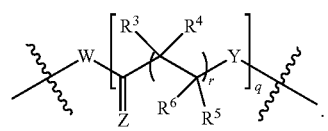

In any or all of the above embodiments, the polymeric material has a formula

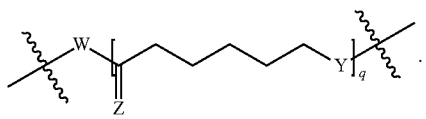

In any or all of the above embodiments, the polymeric material selected from polycaprolactone, polycaprolactone diol, polycaprolactone triol, polycaprolactone-block-polytetrahydrofuan-block polycaprolactone, poly(ethylene oxide)-block-polycaprolactone, poly(ethylene glycol)-block-poly(e-caprolactone) methyl ether, and combinations thereof.

In any or all of the above embodiments, the polymeric material is polycaprolactone having a molecular weight of 25,000 g/mol.

In any or all of the above embodiments, the polymeric coating comprises polylactic acid or polyvinyl chloride.

In any or all of the above embodiments, the one or more fluidic channels are microfluidic channels.

In any or all of the above embodiments, the one or more fluidic channels are surface-lateral flow fluidic channels.

In any or all of the above embodiments, the one or more fluidic channels are fluidly coupled to a sample pre-treatment area, a flow-through channel, or a combination thereof.

In any or all of the above embodiments, a plurality of fluidic channels are present on the first surface of the substrate, the second surface of the substrate, or both.

In any or all of the above embodiments, the one or more fluidic channel comprises varying widths.

In any or all of the above embodiments, the one or more fluidic channels comprise a first portion having a first width and a second portion fluidly coupled to the first portion, wherein the second portion has a second width, the second width being wider than the first width of the first portion.

In any or all of the above embodiments, a plurality of fluidic channels are present on both the first and second surfaces of the substrate and the plurality of fluidic channels have the same configuration and dimensions on each of the first and second surfaces.

In any or all of the above embodiments, the one or more polymer inclusion membrane spots comprise a complexation agent, a transfer enhancer component, a polymeric material, or a combination thereof.

In any or all of the above embodiments, the complexation agent is selected from 1-(2-pyridylazo)-2-naphthol, 1-(2-thiazolylazo)-2-naphthol, 2-(2-pyridylazo)-1-naphthol, 4-(2-pyridylazo)-1-naphthol, 4-(50Chloro-2-pyridylazo)-1,3-diaminobenzene, 4-(2-pyridylazo)resorcinol, or 4-(2-thiazolylazo)resorcinol, 2-(2-thiazolylazo)-5-d imethylaminophenol, glyoxal bis(2-hydroxyanil), o-salicylideneaminophenol, 3-hydroxypicolinaldehyde azine, chloranilic acid, N-benzoyl-N-phenlhydroxylamine, o,o-dihydroxyarylazo compounds, azoazoxy BN, tiron, catechol, or combinations thereof.

In any or all of the above embodiments, the transfer enhancer component is selected from (R,R)—(−)-N,N'-Bis (3,5-di-tert-butylsalicylidene)-1,2-cyclohexanediamine, a salen ligand, an acac ligand, nitrilotriacetic acid, bipyridine, 1,3-diphenylguanidine, diantipyrylmethane, immobilized ethylenediaminetetraacetic acid, or derivatives or combinations thereof.

In any or all of the above embodiments, the polymeric material is the polymeric material according to any or all of the above embodiments.

In any or all of the above embodiments, the polymer inclusion membrane spots are positioned within the one or more fluidic channels in a linear pattern.

In any or all of the above embodiments, the polymer inclusion membrane spots have a volume ranging from 1 nL to 25 µL.

In any or all of the above embodiments, the polymer inclusion spots are separated by a distance ranging from 250 µm to 2 mm.

In any or all of the above embodiments, the polymer inclusion spots are separated by a distance ranging from 5 nm to 250 µm.

In any or all of the above embodiments, the substrate is surface modified with a silyl reagent.

Also disclosed herein are embodiments of fluidic devices, comprising two or more substrates, wherein each substrate is coated with a polymer inclusion membrane spot and each substrate has a different pH values; and a fluidic channel-containing substrate configured to house the two or more substrates and that comprises a fluidic channel that fluidly connects the two or more substrates.

In any or all embodiments, the device further comprises a fluidic platform configured to house the plurality of substrates, a first layer of a polymer-coated substrate, and a second layer of a polymer-coated substrate.

Also disclosed here are embodiments of a multidimensional fluidic device, comprising a substrate that is coated or substantially coated with a polymeric material and that comprises a first surface and a second surface; a flow-through spot formed in the substrate that extends from the first surface to the second surface of the substrate; a fluidic channel formed in second surface of the substrate; a polymer inclusion membrane spot deposited on the first surface of the substrate near the flow-through spot.

Methods for making fluidic devices also are disclosed. In some embodiments, the method comprises depositing one or more polymer inclusion membrane spots onto a surface of a substrate; placing one or more masks on at least one surface of the substrate to form a masked substrate; fabricating at least one fluidic channel pattern in the one or more masks; exposing the masked substrate to an exposure medium; and removing the one or more masks.

In any or all embodiments, the one or more polymer inclusion membrane spots are deposited onto the surface of the substrate in a linear pattern.

In any or all of the above embodiments, the one or more polymeric inclusion membrane spots are deposited as a square, rectangular, circular, or ellipsoidal shape.

In any or all of the above embodiments, the one or more polymer inclusion membrane spots are deposited by hand or by an ink-jet printer.

In any or all of the above embodiments, the one or more masks are adhered to the at least one surface of the substrate using an adhesive.

In any or all of the above embodiments, the one or more masks comprise an adhesive that adheres to the at least one surface of the substrate upon contact.

In any or all of the above embodiments, the one or more masks are placed on a first surface of the substrate, a second surface of the substrate, or both.

In any or all of the above embodiments, the at least one fluidic channel pattern is fabricated in the one or more masks before the one or more masks are placed on the at least one surface of the substrate.

In any or all of the above embodiments, the at least one fluidic channel pattern is fabricated in the one or more masks after the one or more masks are placed on the at least one surface of the substrate.

In any or all of the above embodiments, two masks are used.

In any or all of the above embodiments, the at least one fluidic channel pattern is fabricated in one of the two masks.

In any or all of the above embodiments, a first different fluidic channel pattern is fabricated in one of the two masks and a second fluidic channel pattern is fabricated in the other of the two masks.

In any or all of the above embodiments, the at least one fluidic channel pattern is fabricated in the one or more masks so as to accommodate the one or more polymer inclusion membrane spots within dimensions of the at least one fluidic channel pattern.

In any or all of the above embodiments, the at least one fluidic channel pattern is fabricated in the one or more masks before deposition of the one or more polymer inclusion membrane spots.

In any or all of the above embodiments, the at least one fluidic channel pattern is fabricated so as to have a single width.

In any or all of the above embodiments, the at least one fluidic channel pattern is fabricated so as to have a plurality of varying widths.

In any or all of the above embodiments, a plurality of fluidic channel patterns are fabricated in the one or more masks.

In any or all of the above embodiments, the exposure medium is a medium comprising oxygen radicals.

In any or all of the above embodiments, the masked substrate is exposed to the exposure medium for at least 8 seconds.

In any or all of the above embodiments, the methods can further comprise coating or substantially coating the substrate with a polymeric material.

In any or all of the above embodiments, the methods can further comprise surface-modifying the substrate by exposing the substrate to a silyl reagent.

In any or all of the above embodiments, the methods can further comprise drying the polymer inclusion membrane composition.

In any or all of the above embodiments, the methods can further comprise creating one or more flow-through spots in the substrate.

In any or all of the above embodiments, the methods can further comprise contacting the fluidic device with a buffer.

In some embodiments, the methods of making a fluidic device comprise coating or substantially coating a substrate with a polymeric material; surface-modifying the substrate by exposing the substrate to a silyl reagent; depositing on a first surface of the substrate a plurality of polymer inclusion membrane spots; placing a first mask on the first surface of the substrate and a second mask on a second surface of the substrate to form a masked substrate, wherein the first mask comprises a fluidic channel; exposing the masked substrate to oxygen radicals; and removing the first mask and second mask to provide the fluidic device.

In any or all of the above embodiments, coating or substantially coating comprises dipping, spraying, or spin-coating the substrate in or with the polymeric material.

Also disclosed herein are methods of using the fluidic devices that comprise contacting a fluidic device according to any or all of the above embodiments with a sample by adding the sample to the at least one fluidic channel pattern of the fluidic device.

In any or all of the above embodiments, the method further comprises counting a number of the polymer inclusion membrane spots that exhibit a color change upon contact with the sample, counting a number of colored spots formed in an area between the polymer inclusion membrane spots, or a combination thereof.

In any or all of the above embodiments, counting the number of the polymer inclusion membrane spots that exhibit a color change upon contact with the sample and/or counting a number of colored spots formed in an area between the polymer inclusion membrane spots correlates to a concentration of metal ions present in the sample.

In any or all of the above embodiments, the color change and/or the colored spots formed between the polymer inclusion membrane spots correlates to an identity of metal ions in the sample.

In any or all of the above embodiments, the sample is an aqueous sample comprising metal ions.

In any or all of the above embodiments, certain metal ion species of the aqueous sample react with the polymer inclusion membrane spots to form a coordination complex that produces the color change.

In any or all of the above embodiments, certain metal ion species of the aqueous sample react with the polymer inclusion membrane spots to form a coordination complex that is soluble in the aqueous sample.

In any or all of the above embodiments, the certain metal ion species are $Co^{2+}$ ions.

In any or all of the above embodiments, the certain metal ion species are $Cu^{2+}$ ions.

In any or all of the above embodiments, the method further comprises using a color filter to selectively visualize certain metal ions.

Also disclosed herein are embodiments of methods for identifying and quantifying metal ions present in an aqueous sample, comprising contacting a fluidic device with an aqueous sample, wherein the fluidic device comprises a polycaprolactone-coated substrate having a first surface and a second surface; one or more fluidic channels defined on the first surface of the polycaprolactone-coated substrate, the second surface of the polycaprolactone-coated substrate, or both; and one or more polymer inclusion membrane spots comprising 1-(2-pyridylazo)-2-naphthol, from (R,R)—(−)—N,N'-Bis(3,5-di-tert-butylsalicylidene)-1,2-cyclohexanediamine, and polycaprolactone positioned within the one or more fluidic channels; adjusting the pH of the aqueous sample using a buffer, or surface-modifying the polycaprolactone-coated substrate with a silyl reagent; and counting a number of polymer inclusion membrane spots that change color upon exposure to the aqueous sample, counting a number of colored spots that appear in spaces between the polymer inclusion membrane spots, or a combination thereof.

In view of the many possible embodiments to which the principles of the present disclosure may be applied, it should be recognized that the illustrated embodiments are only preferred examples and should not be taken as limiting the scope of the claimed invention. Rather, the scope is defined by the following claims.

We claim:

1. A fluidic device, comprising:
   a substrate having a first surface and a second surface;
   one or more fluidic channels defined on the first surface of the substrate, the second surface of the substrate, or both the first surface and the second surface of the substrate;
   a plurality of discrete polymer inclusion membrane spots positioned within at least one of the one or more fluidic channels, wherein the discrete polymer inclusion membrane spots of the plurality are positioned along a length of the at least one fluidic channel; and
   a buffer that is deposited on one or more of the discrete polymer inclusion membrane spots of the plurality.

2. The fluidic device of claim 1, wherein the substrate is a single-layered hydrophilic, porous substrate comprising a polymeric coating or the substrate is single-layered a hydrophobic, porous substrate.

3. The fluidic device of claim 2, wherein the polymeric coating comprises polylactic acid or polyvinyl chloride.

4. The fluidic device of claim 2, wherein the polymeric coating comprises a polymer material having a structure satisfying a formula

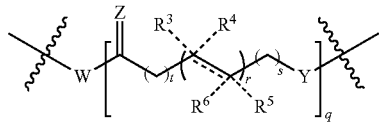

wherein Z, Y, and W independently are selected from O, S, NH, and $NR^2$, where $R^2$ is selected from hydrogen, aliphatic, aryl, and heteroaryl; $R^3$, $R^4$, $R^5$, and $R^6$ (if present) independently are selected from hydrogen, aliphatic, aryl, heteroaryl, and a heteroatom-containing moiety selected from halogen, aldehyde (—$R^aCHO$), acyl halide (—$R^aC(O)X$) (where X is selected from fluorine, chlorine, bromine, and iodine), carbonate (—$R^aOC(O)OR^b$), carboxyl (—$R^aC(O)OH$), carboxylate (—$R^aCOO^-$), ether (—$R^aOR^b$), ester (—$R^aC(O)OR^b$, or —$R^aOC(O)R^b$), hydroxyl (—$R^aOH$), ketone (—$R^aC(O)R^b$), silyl ether ($R^bR^cR^dSiOR^a$—), peroxy (—$R^aOOR^b$), hydroperoxy (—$R^aOOH$), phosphate (—$R^aOP(O)(OH)_2$), phosphoryl (—$R^aP(O)(OH)_2$), phosphine (—$PR^aR^bR^c$), thiol (—$R^aSH$), thioether/sulfide (—$R^aSR$), disulfide (—$R^aSSR^b$), sulfinyl (—$R^aS(O)R^b$), sulfonyl (—$R^aSO_2R^b$), carbonothioyl (—$R^aC(S)R^b$ or —$R^aC(S)H$), sulfino (—$R^aS(O)OH$), sulfo (—$RaSO_3H$), thiocyanate (—$R^aSCN$), isothiocyanate (—$R^aNCS$), oxazole, oxadiazole, imidazole, triazole, tetrazole, amide (—$R^aC(O)NR^bR^c$, or —$R^aNR^bC(O)R^c$), azide ($N_3$), azo (—$R^aNNR^b$), cyano (—$R^aOCN$), isocyanate (—$R^aNCO$), imide (—$R^aC(O)NR^bC(O)R^c$), nitrile (—$R^aCN$), isonitrile (—$R^aN^+C^-$), nitro (—$R^aNO_2$), nitroso (—$R^aNO$), nitromethyl (—$R^aCH_2NO_2$), and amine (—$R^aNH_2$, —$R^aNHR^b$, —$R^aNR^bR^c$), wherein $R^a$ is absent, aliphatic, aryl, heteroaliphatic, or heteroaryl; $R^b$, $R^c$, and $R^d$ independently are hydrogen, aliphatic, aryl, heteroaliphatic, heteroaryl, and any combination thereof; r is from 1 to 4; s and t independently range from 0 to about 4; and q ranges from at least 1 to about 1000.

5. The fluidic device of claim 4, wherein the polymeric material is selected from polycaprolactone, polycaprolactone diol, polycaprolactone triol, polycaprolactone-block-polytetrahydrofuan-block polycaprolactone, poly(ethylene oxide)-block-polycaprolactone, poly(ethylene glycol)-block-poly(e-caprolactone) methyl ether, or combinations thereof.

6. The fluidic device of claim 1, wherein the at least one fluidic channel that comprises the discrete polymer inclusion membrane spots is a microfluidic channel, and any other fluidic channels are selected from microfluidic channels, flow-through channels, surface-lateral flow fluidic channels, or a combination thereof, and wherein the microfluidic channel comprising the discrete polymer inclusion membrane spots and the other one or more fluidic channels are fluidly coupled to a sample pre-treatment area, a flow-through channel, or a combination thereof.

7. The fluidic device of claim 2, wherein a plurality of fluidic channels are present on the first surface of the substrate, the second surface of the substrate, or both the first surface and the second surface of the substrate, and wherein each of the fluidic channels of the plurality comprises varying widths.

8. The fluidic device of claim 7, wherein each of the fluidic channels of the plurality comprises a first portion having a first width and a second portion fluidly coupled to the first portion, wherein the second portion has a second width, the second width being wider than the first width.

9. The fluidic device of claim 1, wherein a plurality of fluidic channels are present on both the first and second surfaces of the substrate and the plurality of fluidic channels have the same configuration and dimensions on each of the first and second surfaces.

10. The fluidic device of claim 1, wherein the discrete polymer inclusion membrane spots independently comprise a complexation agent selected from 1-(2-pyridylazo)-2-naphthol, 1-(2-thiazolylazo)-2-naphthol, 2-(2-pyridylazo)-1-naphthol, 4-(2-pyridylazo)-1-naphthol, 4-(5-chloro-2-pyridylazo)-1,3-diaminobenzene, 4-(2-pyridylazo) resorcinol, 4-(2-thiazolylazo)resorcinol, 2-(2-thiazolylazo)-5-di methylaminophenol, glyoxal bis(2-hydroxyanil), o-salicylidene-aminophenol, 3-hydroxypicolinaldehyde azine, chloranilic acid, N-benzoyl-N-phenlhydroxylamine, o,o'-dihydroxyarylazo compounds, azoazoxy BN, tiron, catechol, or combinations thereof; a transfer enhancer component selected from (R,R)-(−)-N,N'-Bis(3,5-di-tert-butylsalicylidene)-1,2-cyclohexanediamine, a salen ligand, an acac ligand, nitrilotriacetic acid, bipyridine, 1,3-diphenylguanidine, diantipyrylmethane, immobilized ethylenediaminetetraacetic acid, or derivatives or combinations thereof; and a polymeric material.

11. The fluidic device of claim 1, wherein the discrete polymer inclusion membrane spots are positioned within the at least one fluidic channel in a linear pattern and are spaced apart such that an empty space exists between each of the discrete polymer inclusion membrane spots.

12. The fluidic device of claim 1, wherein the substrate is surface modified with a silyl reagent.

13. A method for making the fluidic device of claim 1, comprising:
depositing the plurality of discrete polymer inclusion membrane spots onto the substrate, wherein the substrate is (i) a single-layered hydrophilic, porous substrate, or (ii) a single-layered hydrophobic, porous substrate;
depositing the buffer on one or more of the discrete polymer inclusion membrane spots of the plurality;
placing one or more masks on the first surface of the substrate, the second surface of the substrate, or both the first surface and second surface of the substrate to form a masked substrate;
fabricating at least one fluidic channel pattern in the one or more masks;
exposing the masked substrate to an exposure medium comprising oxygen radicals; and
removing the one or more masks.

14. The method of claim 13, wherein the plurality of discrete polymer inclusion membrane spots are deposited, by hand or by using an ink-jet printer, onto the substrate in a linear pattern and having a square, rectangular, circular, or ellipsoidal shape.

15. The method of claim 13, wherein the at least one fluidic channel pattern is fabricated in the one or more masks before the one or more masks are placed on the at least one surface of the substrate or after the one or more masks are placed on the at least one surface of the substrate.

16. The method of claim 13, wherein two masks are used and wherein the at least one fluidic channel pattern accommodates the plurality of discrete polymer inclusion membrane spots within dimensions of the at least one fluidic channel pattern and wherein other fluidic channels are fabricated in one of the two masks, or in both of the two masks.

17. The method of claim 13, wherein the at least one fluidic channel pattern is fabricated so as to have a single width or a plurality of varying widths.

18. The method of claim 13, further comprising:
(i) coating or substantially coating the first surface, the second surface, or both the first surface and the second surface of the substrate with a polymeric material;
(ii) surface-modifying the first surface, the second surface, or both the first surface and the second surface of the substrate by exposing the substrate to a silyl reagent;
(iii) drying the plurality of discrete polymer inclusion membrane spots;
(iv) creating one or more flow-through spots in the substrate; or
any combination of (i) to (iv).

19. A method, comprising contacting the fluidic device according to claim 1 with a sample by adding the sample to the at least one fluidic channel comprising the discrete polymer inclusion membrane spots.

20. The method of claim 19, further comprising (i) counting a number of the discrete polymer inclusion membrane spots that exhibit a color change upon contact with the sample, (ii) counting a number of colored spots formed in an area between the discrete polymer inclusion membrane spots, or (iii) a combination thereof, and wherein the color change and/or the colored spots formed between the discrete polymer inclusion membrane spots correlates to an identity of metal ions species in the sample.

21. The method of claim 20, wherein the metal ion species are $Co^{2+}$ ions, $Cu^{2+}$ ions, or a combination thereof.

* * * * *